(12) United States Patent
Wiederin

(10) Patent No.: US 7,469,606 B1
(45) Date of Patent: Dec. 30, 2008

(54) AUTOMATED SAMPLING DEVICE

(75) Inventor: Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

(21) Appl. No.: 11/701,889

(22) Filed: Feb. 2, 2007

Related U.S. Application Data

(63) Continuation-in-part of application No. 11/590,305, filed on Oct. 31, 2006, which is a continuation-in-part of application No. 10/966,888, filed on Oct. 15, 2004, now Pat. No. 7,201,072.

(60) Provisional application No. 60/604,548, filed on Aug. 26, 2004.

(51) Int. Cl.
    *G01N 1/00* (2006.01)
(52) U.S. Cl. .................................. 73/864.24
(58) Field of Classification Search ............... 73/864.24
    See application file for complete search history.

(56) References Cited

U.S. PATENT DOCUMENTS

| 5,876,668 A * | 3/1999 | Kawashima et al. ............ 422/64 |
| 2002/0106814 A1 * | 8/2002 | Matsubara et al. ............ 436/180 |
| 2005/0059164 A1 * | 3/2005 | Feygin ........................ 436/180 |
| 2005/0095724 A1 * | 5/2005 | Shibutani et al. ............. 436/180 |
| 2006/0088940 A1 * | 4/2006 | Feingold et al. ............... 436/47 |
| 2006/0120922 A1 * | 6/2006 | Matsumoto .................... 422/64 |

* cited by examiner

*Primary Examiner*—Robert R Raevis
(74) *Attorney, Agent, or Firm*—Suiter Swantz pc llo

(57) ABSTRACT

An automated sampling or dispensing device comprising a support surface for supporting a sample holder and a fluid holder, a first arm assembly for supporting a fluid probe comprising a z-axis support and a horizontal fluid probe support arm, a first drive assembly, a second arm assembly for supporting a sample probe comprising a z-axis support and a horizontal sample probe support arm, and a second drive assembly. The first arm assembly is suitable for collecting a fluid from a fluid vessel and transferring it to a sample vessel, the second arm assembly is suitable for collecting an amount of sample and fluid from the sample vessel, and the support surface further comprises a mixing assembly suitable for mixing the fluid and the sample.

19 Claims, 33 Drawing Sheets

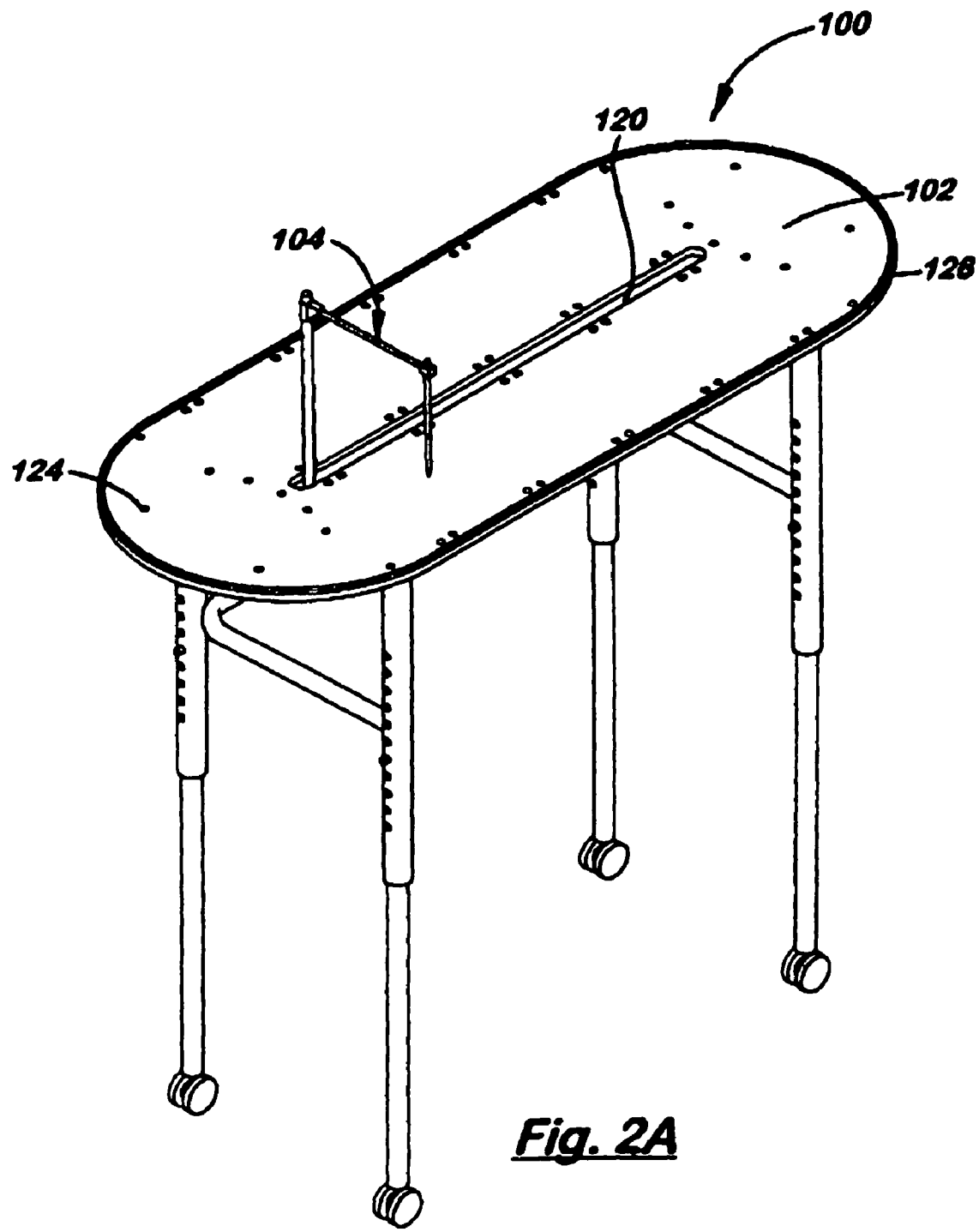

AUTOMATED SAMPLING DEVICE

CROSS REFERENCE

The present application is a continuation-in-part under 35 U.S.C. § 120 of U.S. patent application Ser. No. 11/590,305 filed Oct. 31, 2006, which is a continuation-in-part under 35 U.S.C. § 120 of U.S. patent application Ser. No. 10/966,888 filed Oct. 15, 2004 now U.S. Pat. No. 7,201,072 which in turn claims the benefit under 35 U.S.C. § 119(e) of U.S. Provisional Application Ser. No. 60/604,548, filed Aug. 26, 2004 all three of which are herein incorporated by reference in their entirety.

FIELD OF INVENTION

The present invention relates generally to laboratory instrumentation, particularly automated sampling devices for drawing samples from stationary sample vessels, and more specifically, to a dampening device for an automated sampling/dispensing device.

BACKGROUND OF THE INVENTION

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

While a vast array of autosamplers are currently known and available, the majority of such devices share one common feature, employing robotic-like systems to analyze multiple vessels or containers containing samples in a given time. Many such devices are equipped with a robotic manipulator capable of two types of linear movement, i.e., x-y and vertical which allows the manipulator to access a container, transfer the container from a parent machine, and return the container to the appropriate position in the sample tray. Another common style of autosampler is one which employs robotic movement to move a sample probe above a sample vessel, or, alternatively, employs a moving table or conveyer to move the sample vessels underneath the sample probe.

Although autosamplers presently known in the art have greatly increased the ease and efficiency of assaying multiple samples at a given time, such samplers are disadvantageous in that they are likely to introduce an additional source for sample contamination, allowing for contamination of sample vessels by contaminants which may fall into containers during analysis. Present autosamplers employing mechanical parts may cause dust, or the like, to fall into these containers because of mechanical wear of the devices that either is directly above the containers while they are moving or as the containers themselves move underneath a dispensing pipette. Further, such autosamplers are typically not enclosed exposing the samples to particulates and other matter present in the air. In addition, prior art autosamplers often result in sample loss or sample cross-contamination during assaying due to the sample probe of the autosampler moving rapidly and vibrations associated with such rapid movement. Also, it is often desirable to dilute, spike or add a standard addition to a sample prior to analysis. These procedures generally require an additional machine or analyst to measure an amount of diluent, spike or standard addition and add it to the sample.

What is desired, therefore, is an automated sampling device without any mechanical moving parts positioned above stationary samples thereby removing such possible source of contamination. Further, it is desired that the automated sampling device be protected from the external environment by placing the device in an automated sampling device enclosure. A mechanism which allows an autosampler to move rapidly from sample to sample without affecting sample volume or causing sample cross-contamination is also desired. Also, the ability to dilute, spike or otherwise add a fluid to the sample while on the automated sampling device without requiring extra manpower or machinery is desired.

SUMMARY OF INVENTION

Accordingly, the present invention is directed to an automated sampling or dispensing device. In accordance with a first aspect of the present invention, automated sampling and dispensing device may comprise a support surface for supporting a sample holder and a fluid holder, a first arm assembly comprising a z-axis support and a fluid probe support arm that supports a fluid probe, and a first drive assembly coupled to the z-axis support of the sample arm assembly for powering and positioning the first arm assembly. Device may further comprise a second arm assembly for supporting a sample probe. The second arm assembly comprises a z-axis support and a horizontal support arm, and a second drive assembly coupled to the z-axis support of the second arm assembly for powering and positioning the second arm assembly. The first arm assembly is suitable for collecting an amount of fluid from a fluid container and transferring it to a container holding an amount of sample. Transfer may be accomplished by releasing the amount of fluid into the sample vessel prior to transfer of some of or the entire sample to a remote location for analysis. The second arm assembly is suitable for collecting an amount of sample from the sample holder and transferring the collected sample and fluid to an analyzer. Device further comprises a mixing assembly coupled to the at least one sample vessel suitable for mixing the fluid and sample prior to transfer of a mixed fluid and sample solution to an analyzer.

In accordance with a second aspect of an embodiment of the present invention, an automated sampling or dispensing device is provided. Automated sampling or dispensing device comprises a support surface for supporting a fluid holder and a sample holder, the fluid holder being suitable for holding at least one sample vessel, the sample holder being suitable for holding a sample vessel, an arm assembly for supporting a probe, including a z-axis support and a horizontal probe support arm, a drive assembly coupled to the z-axis support of the arm assembly for powering and positioning the arm assembly, a mixing assembly coupled to the at least one sample vessel. The arm assembly is suitable for collecting a fluid from the fluid vessel and transferring the fluid to the sample vessel, the mixing assembly is suitable for mixing the fluid and the sample in the at least one sample vessel, and collecting an amount of a mixed fluid and sample solution from the at least one sample vessel.

In accordance with an additional aspect of the present invention, a method of sampling or dispensing is provided. Method may comprise providing a fluid vessel suitable for holding a fluid, providing a sample vessel suitable for holding a sample, providing a probe suitable for selectively collecting or depositing at least one of the fluid or the sample, collecting an amount of fluid from the fluid vessel, depositing the amount of fluid into the sample vessel, mixing the amount of fluid and a sample in the sample vessel, collecting a mixed fluid and sample solution; and transporting the mixed fluid and sample solution to an analyzer for analysis.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF DRAWINGS

The numerous objects and advantages of the present invention may be better understood by those skilled in the art by reference to the accompanying figures in which:

FIG. 2A is a partial isometric view of an automated sampling or dispensing device, wherein a center slot in the support surface is present allowing the sample arm assembly to be connected with the drive assembly;

DETAILED DESCRIPTION OF INVENTION

Reference will now be made in detail to the presently preferred embodiments of the invention, examples of which are illustrated in the accompanying drawings.

Figure 1:
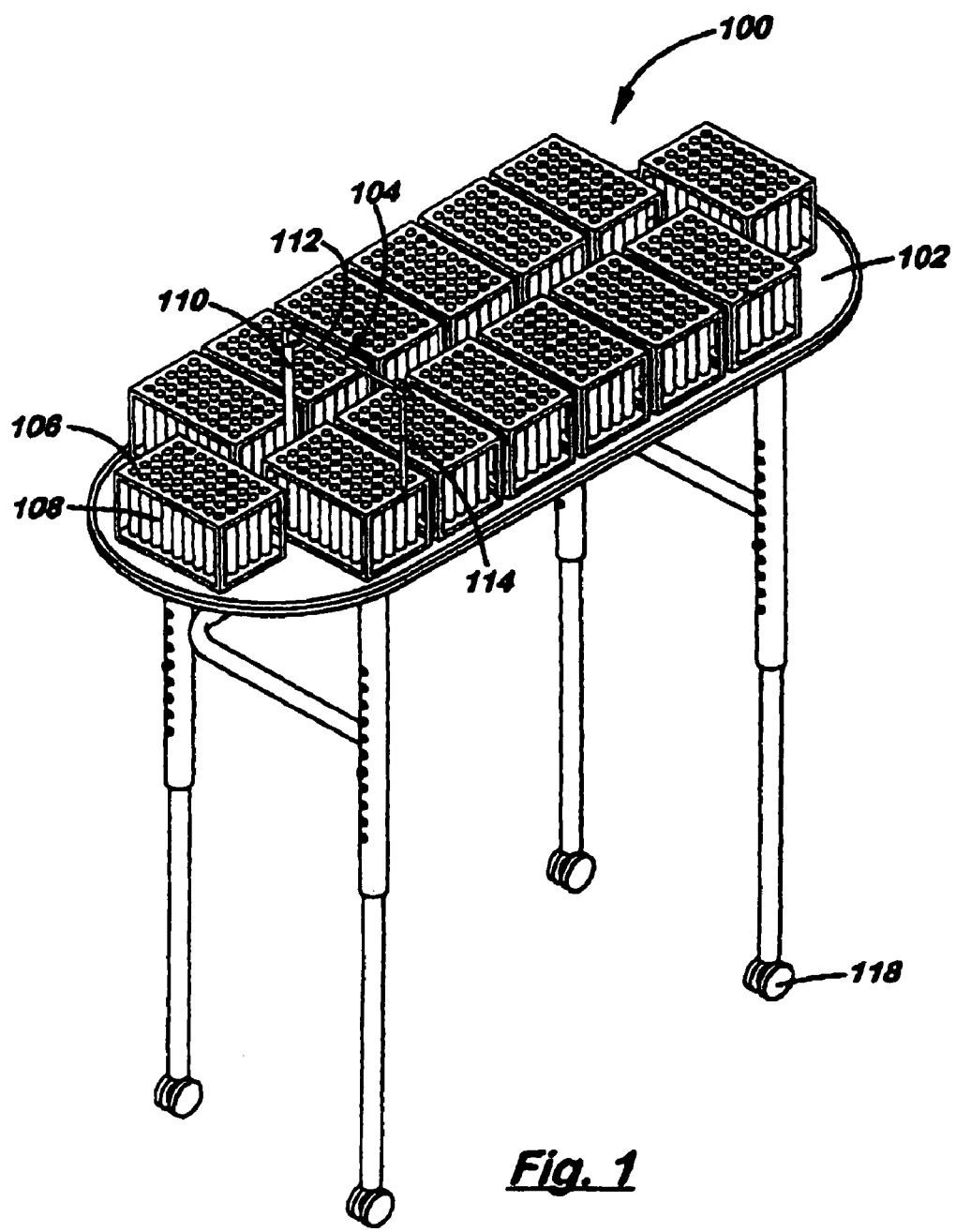
FIG. 1 is an isometric view illustrating an automated sampling or dispensing device in accordance with an exemplary embodiment of the present invention.

FIG. 1 illustrates automated sampling device 100 in accordance with an exemplary embodiment of the present invention. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the exemplary embodiment illustrated) in a given time depending upon test requirements.

In the embodiment illustrated, sample arm assembly 104 includes a z-axis support 110 and a sample probe support arm 112 that supports a sample probe 114. As illustrated, the z-axis which is aligned with gravity or vertical axis. In use, sample probe 114 is mounted to sample probe support arm 112 which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an embodiment, the length of a sample probe support arm (the length of arm extending from the y-rotary axis) is no more than one-half the length of a linear translation of the center slot (i.e. is no more than half of the length of x-axis linear motion). In a preferred embodiment, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional embodiment, the y-rotary axis of an automated sampling device allows for access to sample vessels on either side of the x-axis motion of linear travel (i.e. on either side of the center slot).

In an embodiment, the components of sample arm assembly 104 are formed of carbon composite materials. Further, all exposed surfaces of the sample arm assembly 104 are made from inert or fluoropolymer-covered materials (i.e. Teflon®). It should be understood, however, that the sample arm assembly may be made with any suitable material known in the art, including aluminum, steel, plastic, and the like.

In addition, sample arm assembly 104 is designed to attach to any type of surface support including a table top. Such assembly may be attached to either side of the center slot. In an embodiment, table top 102 may be mounted onto legs with casters 118, rollers and the like. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are utilized. The ability to adjust table top height also allows the automated sampling device to accommodate various sized sample vessels.

Figure 2B:
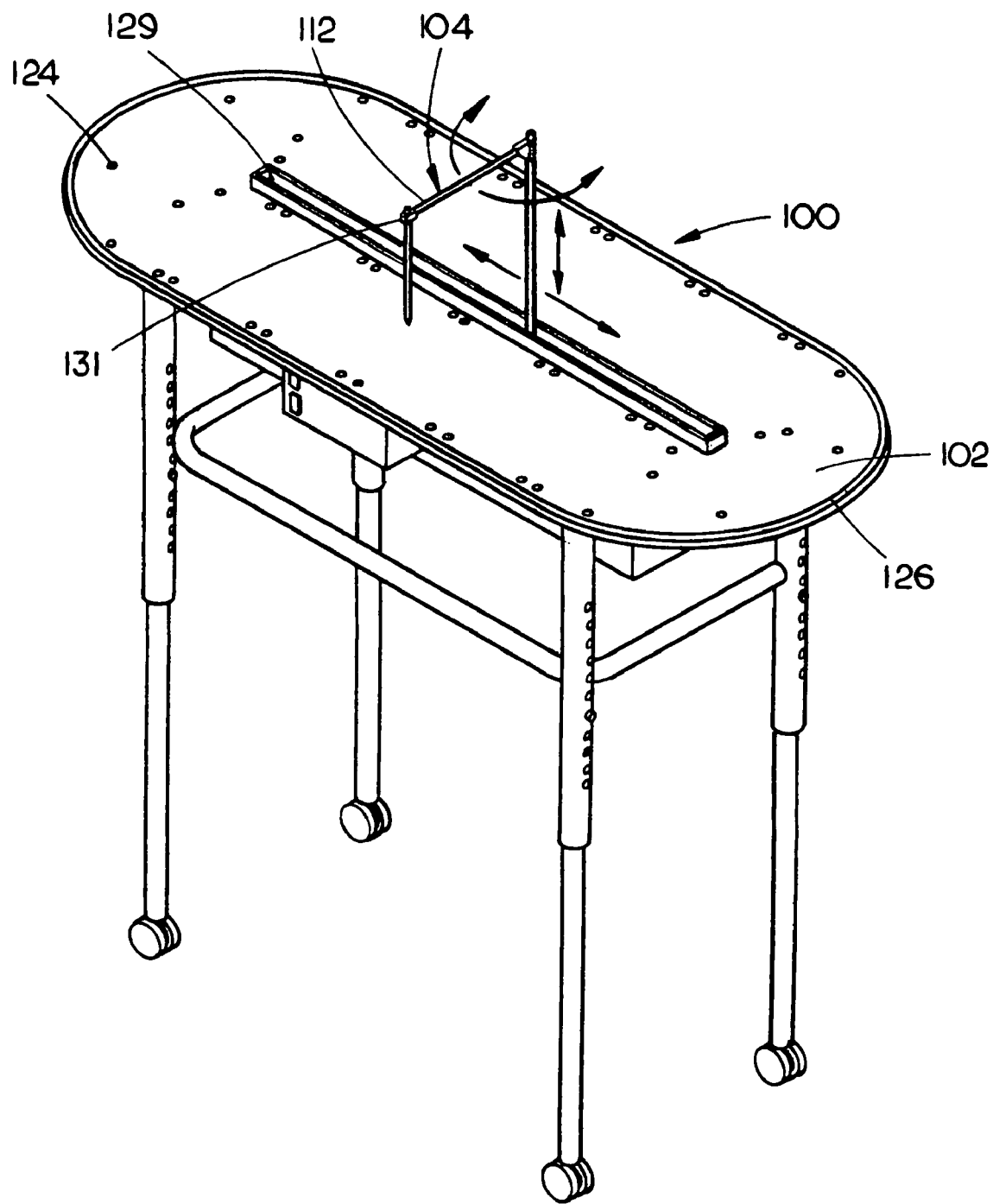
FIG. 2B is a partial isometric view of an automated sampling or dispensing device, wherein a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an embodiment, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage.

In addition to FIG. 2A, FIG. 2B demonstrates an automated sampling or dispensing device including a sample arm assembly 104 attached to the drive assembly 128 via a raised slot 129. In one embodiment, a magnet 131 is attached to the end of the sample probe support arm 112 which allows detection of a three-dimensional position in space wherein the magnet 131 is embedded into the sample probe support arm 112 and is detected by a sensing means such as a Hall Effect sensor.

Figure 3:
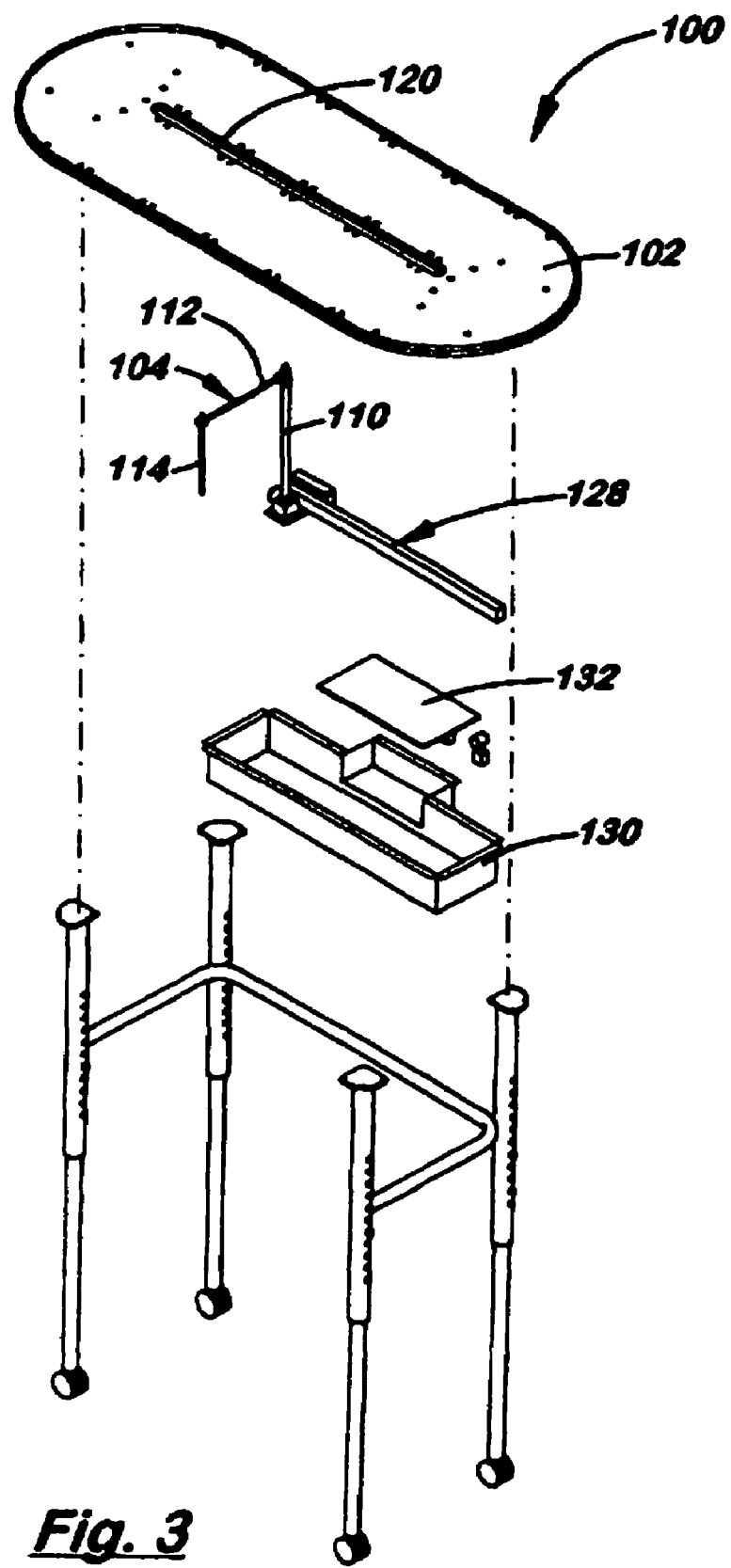
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an embodiment, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without any operator assistance, thereby allowing the operator to perform other tasks. Moreover, it is possible to set-up the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having any mechanical moving parts above stationary samples. Additionally, housing 130 encloses drive assembly 128 to protect the assembly from debris, dust, contaminates, and the like. Housing 130 may be made of any suitable material, e.g. blow molded polyethylene.

Figure 4A:
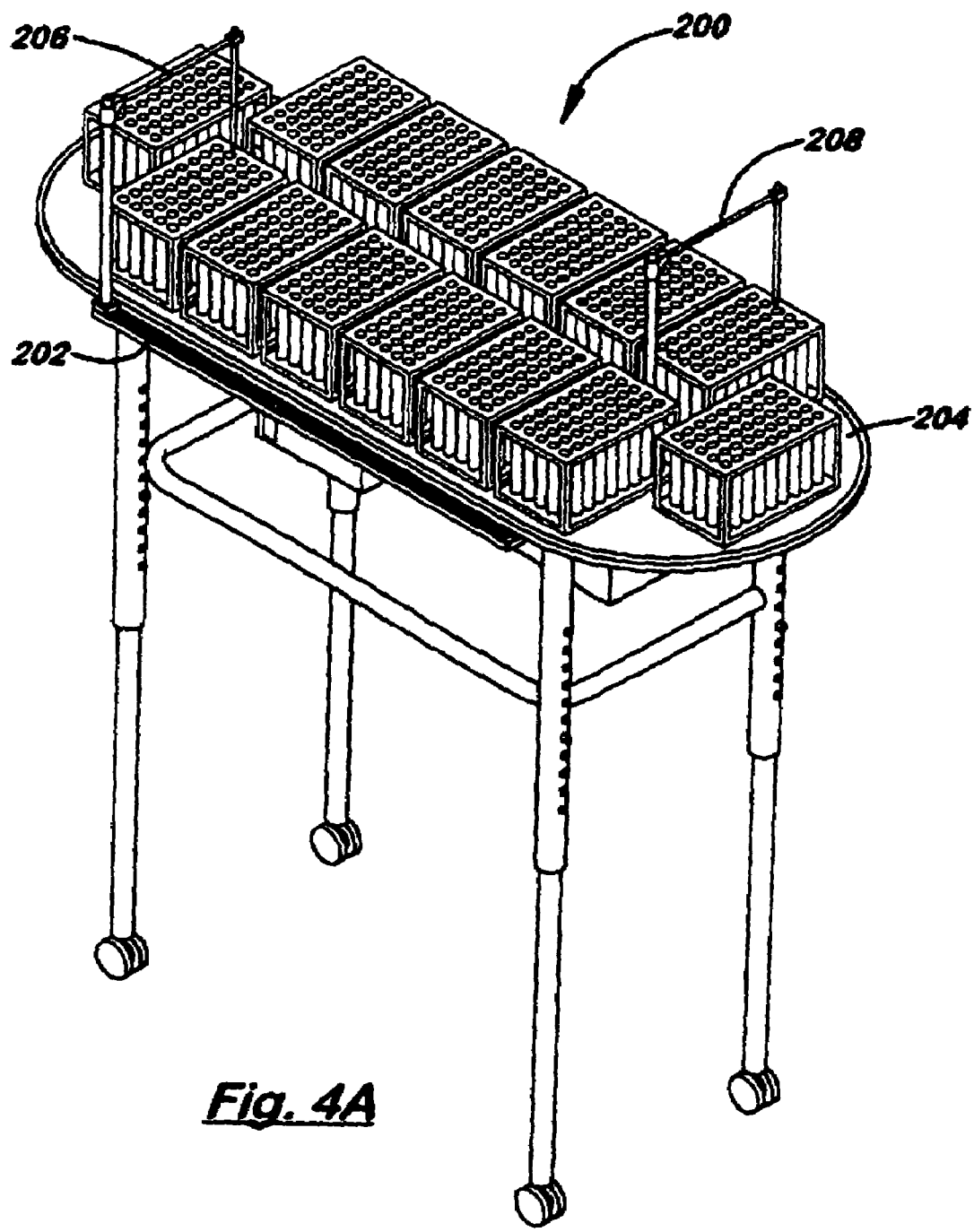
FIG. 4A is an isometric view illustrating an automated sampling or dispensing device in accordance with a second exemplary embodiment of the present invention wherein multiple sampling arm assemblies and drive assemblies are mounted to the top of the support surface of the automated sampling or dispensing device.
Figure 4B:
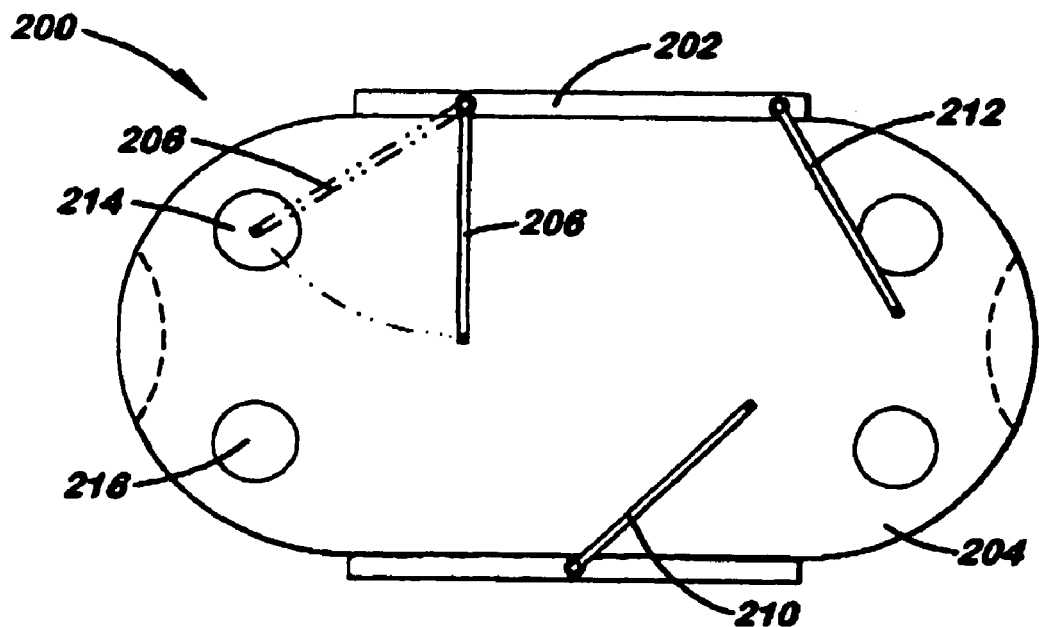
FIG. 4B is plan view illustrating an automated sampling or dispensing device in accordance with the second exemplary embodiment of the present invention, wherein multiple sample arm assemblies and rinse stations are present on one support surface.

FIGS. 4A and 4B illustrate an automated sampling device 200 in accordance with a second exemplary embodiment of the present invention wherein multiple sampling arm assemblies (i.e. sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e. sample arm assembly 206 and 212). Utilization of additional sample arm assemblies allows multiple sample zones to be set up (i.e. prep zone, assaying zone, and the like).

In additional embodiments, various types of multiple rinse or eluent stations may be included in the automated sampling device. For instance, multiple rinse stations (i.e. 214 and 216) of the overflow type designed to reduce the chance of carry-over contamination may be present. Further, overflow rinse stations may contain a series of different chemical rinses to reduce contamination between sample analyses (e.g. surfactant, nitric acid, hydrofluoric acid, and deionized water). For multiple eluent stations, the automated sampling device may contain such stations for step elution from a chromatographic column.

Figure 5:
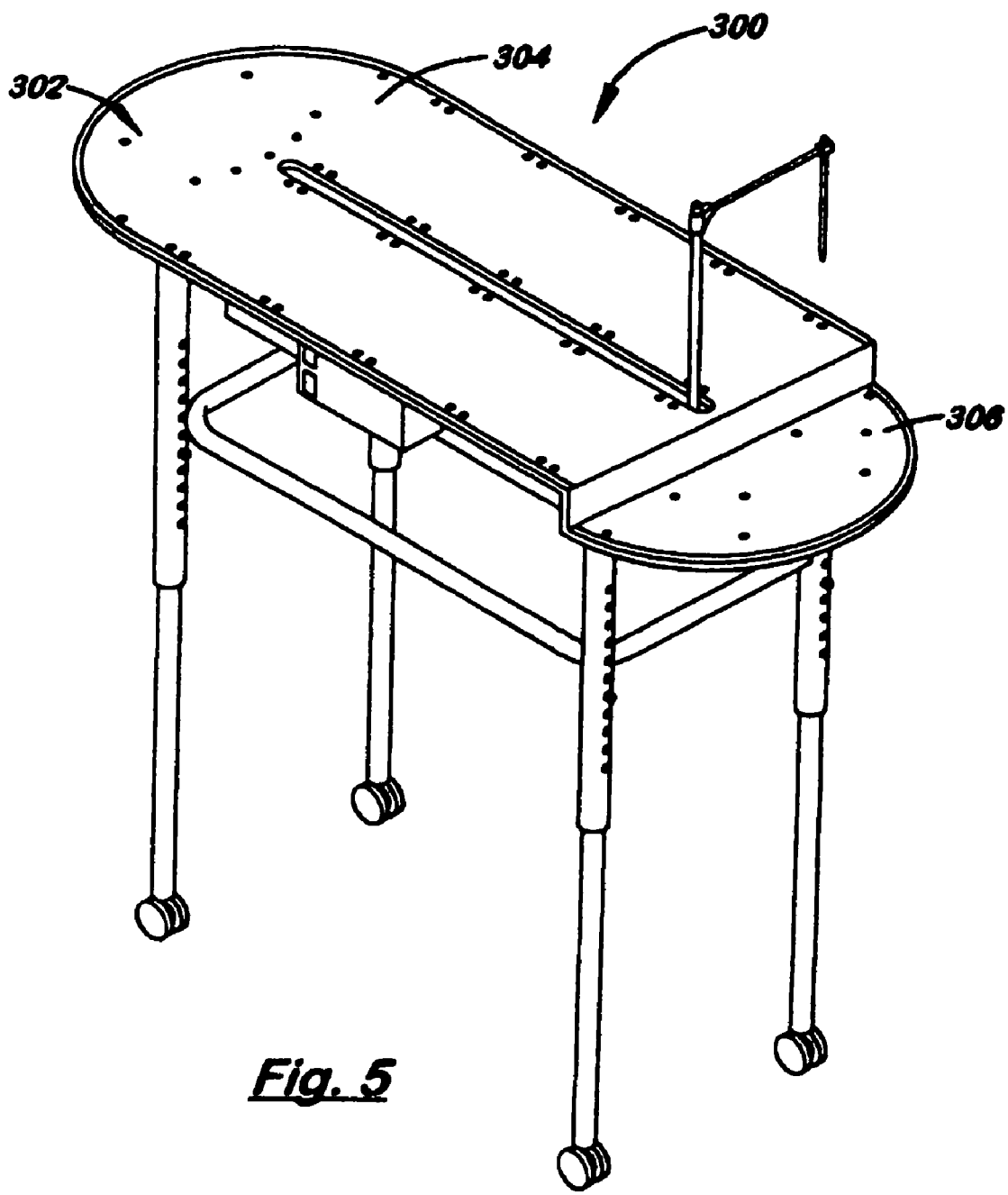
FIG. 5 is an isometric view illustrating an automated sampling or dispensing device in accordance with a third exemplary embodiment of the present invention, wherein the support surface of the automatic sampling or dispensing device is provided with more than one plane.

Referring now to FIG. 5, an automated sampling device in accordance with a third exemplary embodiment of the present invention is disclosed wherein a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 6:
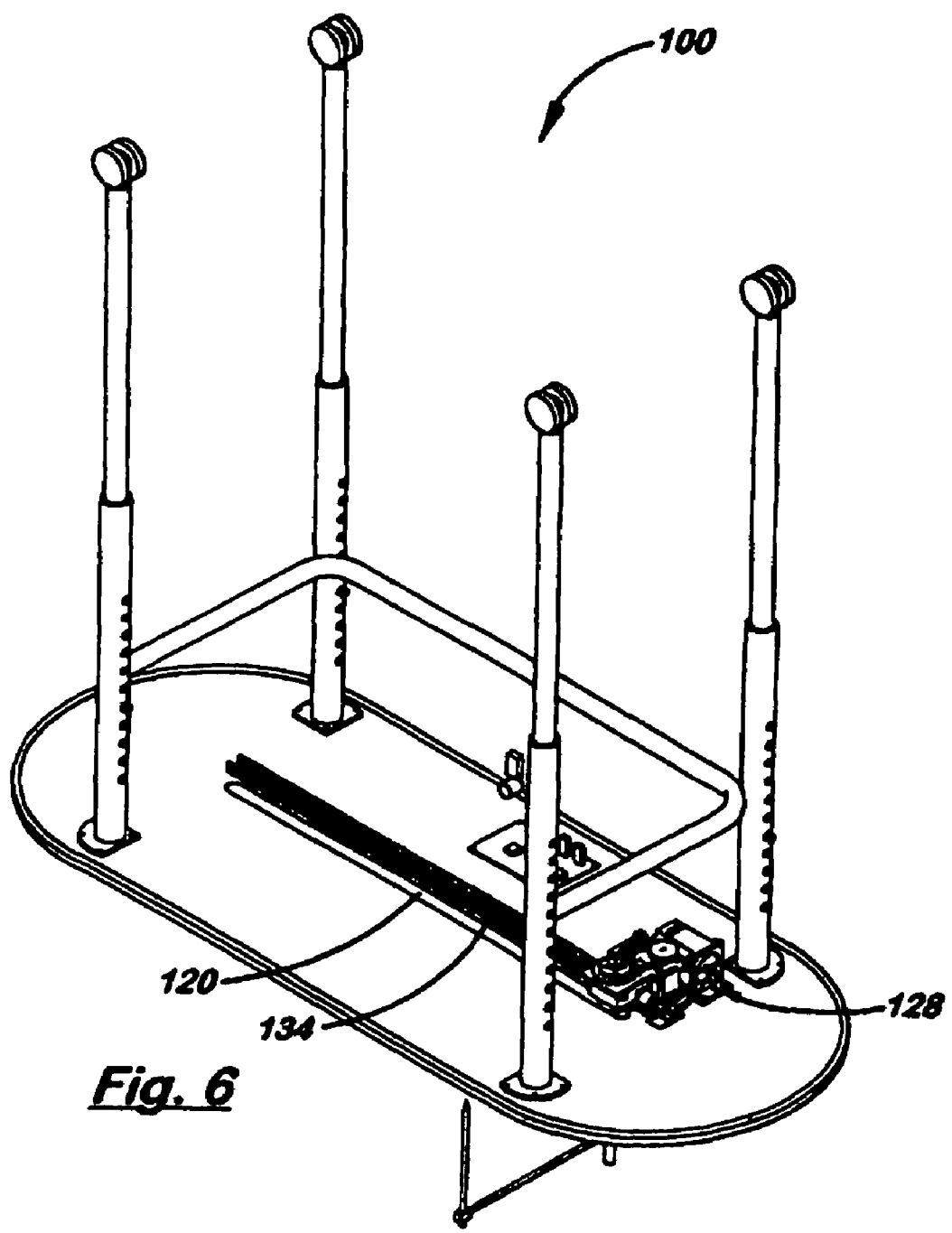
FIG. 6 is an isometric view of the automated sampling or dispensing device shown in FIG. 1, further illustrating the drive assembly.
Figure 7:
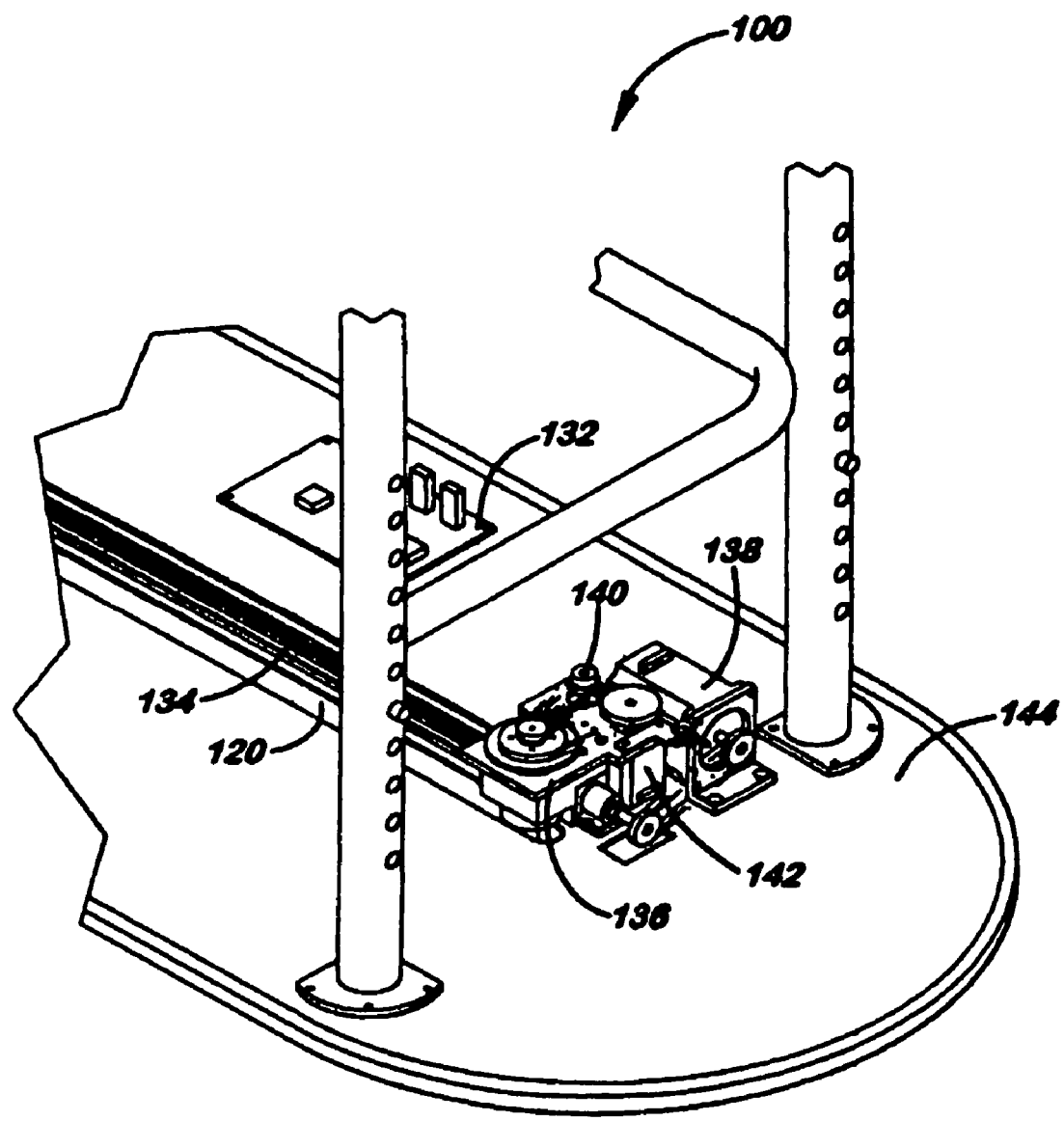
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. First, FIG. 6 provides an overview of a drive assembly in accordance with the present invention depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Any conventional stepper motor known in the art may be used to control translation of the sample arm assembly's movements along center slot 120. Moreover, those of skill in the art will appreciate that any suitable linear drive may be used including a worm drive. Motor two 140 controls angular rotation of a sample arm assembly and is connected to sled 136. In an embodiment, motor two 140 is a radial motor. Motor three 142 controls vertical movement of a sample arm assembly and is attached to sled 136. Any suitable stepper motor may be used for controlling vertical movement of the sample arm assembly. In an additional embodiment, motor three 142 is a slip-clutch system. Further, in accordance with the present invention, the drive assembly may be hard-wired or in the preferred embodiment, controlled via wireless communications. Thus, wireless communications may be utilized to connect controller 132 with the desired analytical instrument (not shown). Utilization of wireless communications allows sample assaying to occur without requiring physical connection with a controller computer increasing mobility of the automated sampling device.

Figure 8:
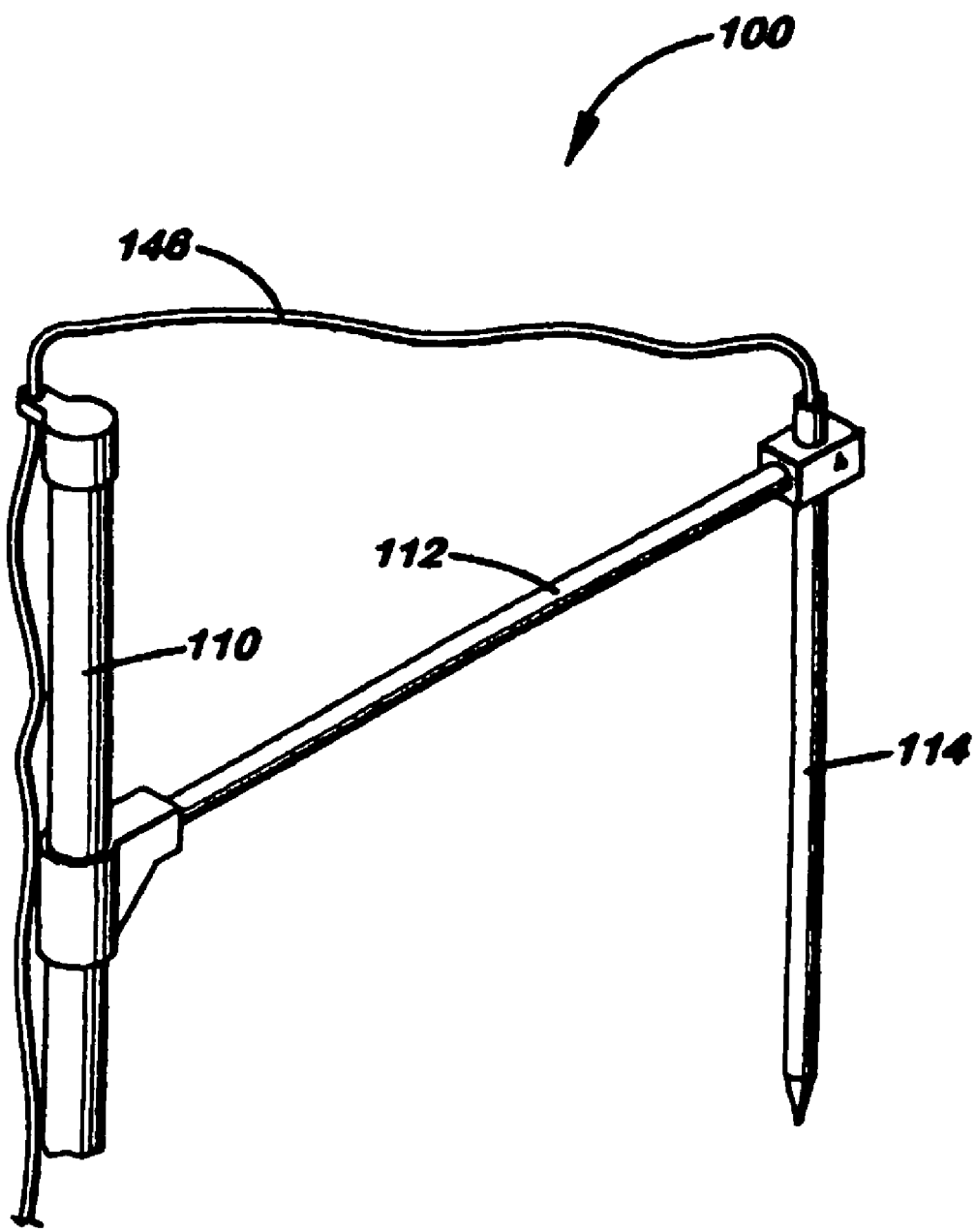
FIG. 8 is a partial isometric view of a sample arm assembly for an automated sampling or dispensing device in accordance with an exemplary embodiment of the present invention.

FIG. 8 provides a detailed depiction of a sample arm assembly of an automated sampling device in accordance with the first exemplary embodiment of the present invention. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an embodiment, the sample arm assembly is attached to the drive assembly via the z-axis support extending through a center slot in the table top; in such embodiment, the drive assembly is attached to a table top bottom. However, it should be understood to those skilled in the art that the drive assembly may be disposed in a variety of locations including on top of the table top without departing from the scope of the present invention.

In an additional embodiment in accordance with the present invention, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g. inductively couple plasma system, mass spectrometer) or a number of other types of vessels (e.g. waste collecting bucket following a wash step). It is further contemplated that the sample tubing may be flexible (as shown) or rigid, comprised of plastic, metal, and the like without departing from the scope and spirit of the present invention. In another embodiment, the automated sampling device may be equipped with one or more independent components for the purpose of sample preparation, sample dilution, addition of standards to samples or sample acidification.

Figure 9A:
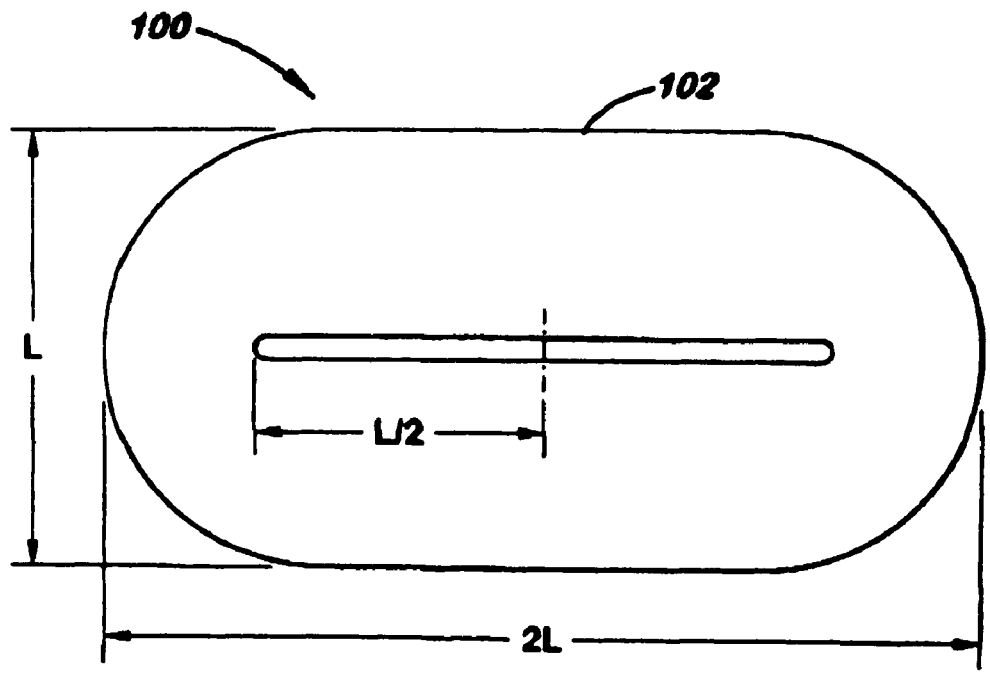
FIG. 9A is plan view illustrating a support surface for use with an automated sampling or dispensing device, wherein the support surface includes a slot and has a footprint in accordance with the first exemplary embodiment of the present invention.
Figure 9B:
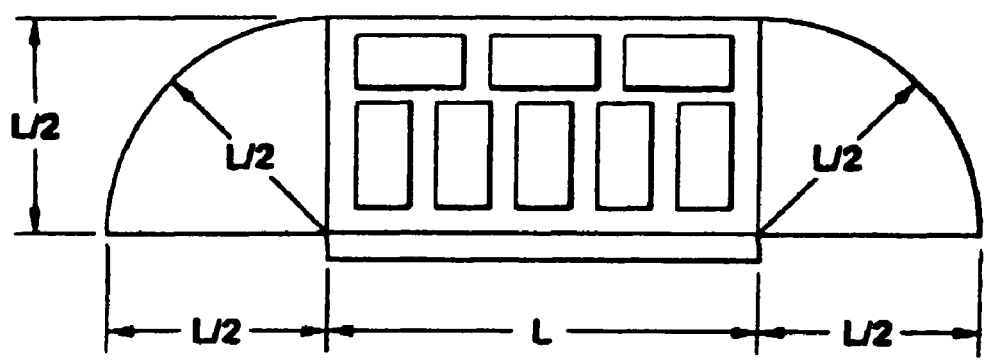
FIG. 9B is plan view illustrating a support surface for use with an automated sampling or dispensing device, in accordance with a fourth exemplary embodiment of the present invention.

Referring to FIGS. 9A and 9B, tables for use with an automated sampling device are described in accordance with exemplary embodiments of the present invention. First, the table 102 includes a slot of length l providing for translation of the sample arm assembly along the length of the table. Further, the table 102 has a footprint for maximizing the usable area of the table 102. As illustrated in FIG. 9A, preferably, the table 102 has a width l substantially equal to the length of the slot l. Moreover, the table 102 is twice as long as the slot, having a length of 2l. Further, the arm length of a sample probe assembly (as shown in FIGS. 1, 2, and 3) is half the length of the slot, having length l/2. This configuration allows for approximately one hundred percent of the footprint of the table to be accessed. In contrast, FIG. 9B illustrates an additional embodiment in accordance with the present invention whereby the table is the shape of a semi-circle and a non-centered slot system is employed.

Figure 10:
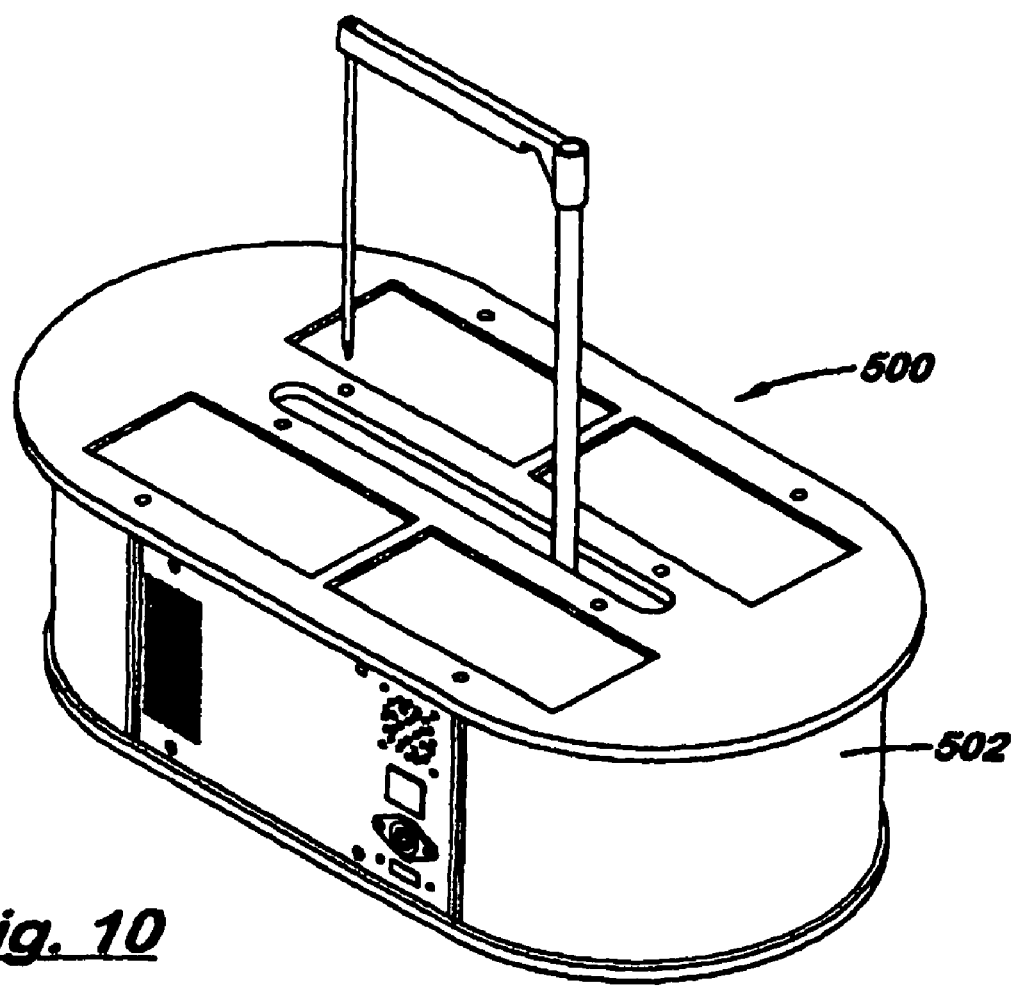
FIG. 10 is an isometric view of an automated sampling or dispensing device in accordance with a fifth exemplary embodiment of the present invention, wherein the device includes a shroud.

Referring to FIG. 10, automated sampling or dispensing device 500 includes a shroud 502. In an exemplary embodiment, the shroud 502 substantially encloses the drive assembly 128 (FIG. 3) for protecting the drive assembly from dust and debris, or preventing dust and debris from the drive assembly from contaminating samples during assaying.

Figure 11:
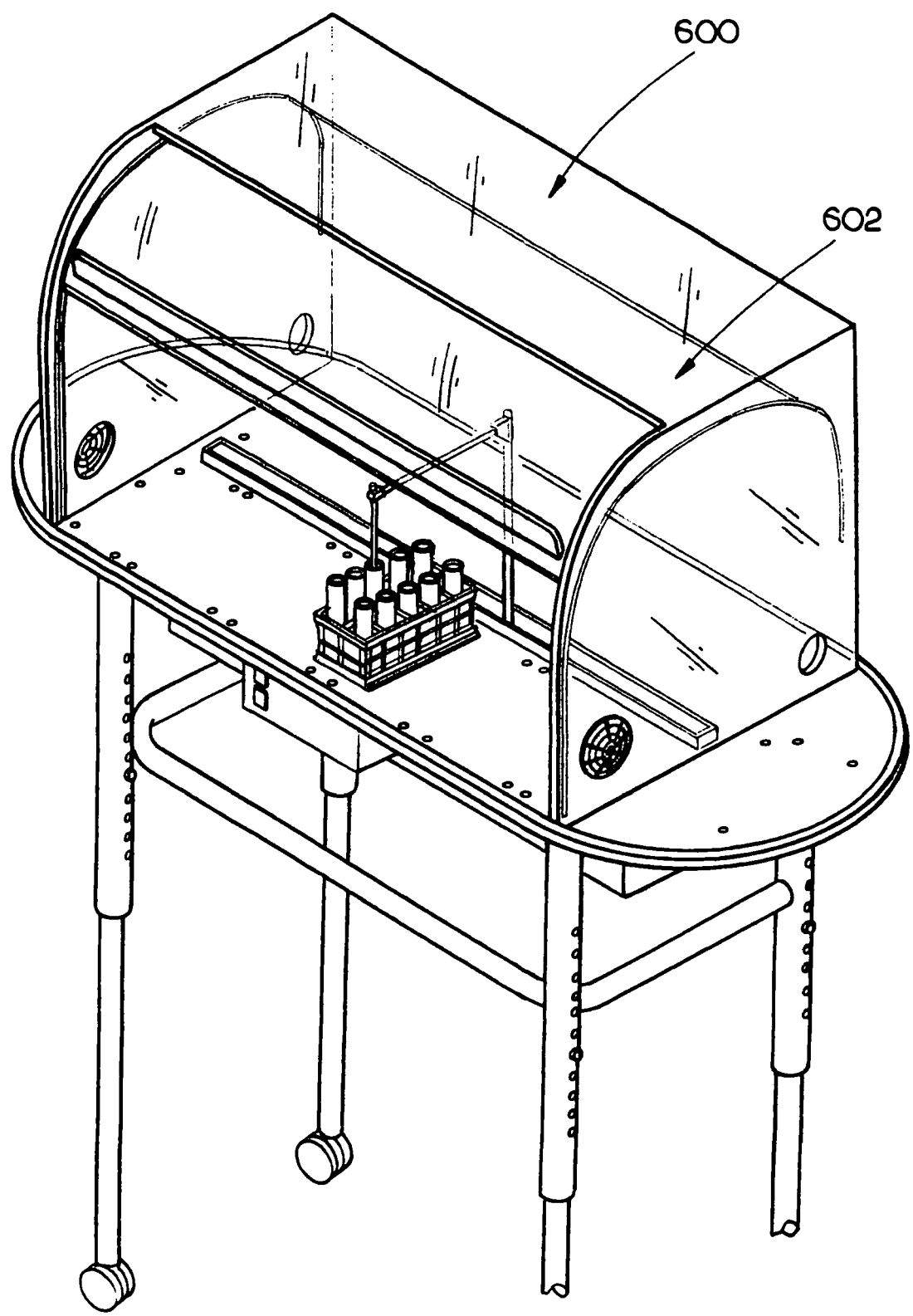
FIG. 11 is an isometric view of an automated sampling or dispensing device in accordance with a sixth exemplary embodiment of the present invention, wherein the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or air-borne substances. In one specific embodiment, the air drawn into the enclosure is passed through a high efficiency particulate air (HEPA) filter. Further, processing of samples which contain hazardous chemicals within a hood allows such samples to be processed without further exposing the user to such chemicals during processing.

Referring to FIGS. 12 through 19 generally, numerous embodiments of an enclosure for an automated sampling/ dispensing device are provided. In general, the enclosure includes at least one support member. The support member is generally perpendicular to a support surface on which the automated sampling/dispensing device is mounted. Further, a lid is mechanically coupled to the at least one support member for covering the support surface on which the automated sampling/dispensing device is mounted. Additionally, at least one flexible sheet is operationally coupled to at least one of the lid or the at least one support member. The at least one support member may provide support to both the lid as well as the at least one flexible sheet. The at least one support member, lid, and at least one flexible sheet enclose the automated sampling device while allowing access to the device by retracting the at least one flexible sheet.

The presently disclosed exemplary enclosures may minimize user exposure to the enclosed samples by allowing the containment of potentially hazardous chemicals within such enclosure. Further, the use of at least one flexible panel allows the enclosure to be shipped efficiently for the enclosure may be disassembled into smaller pieces and thus, be shipped in a smaller box when compared to enclosures with non-flexible panels/doors. Moreover, the use of the at least one flexible panel allows the enclosure to be shaped to accommodate varying shaped automated sampling and or dispensing devices and assemblies.

Figure 12:
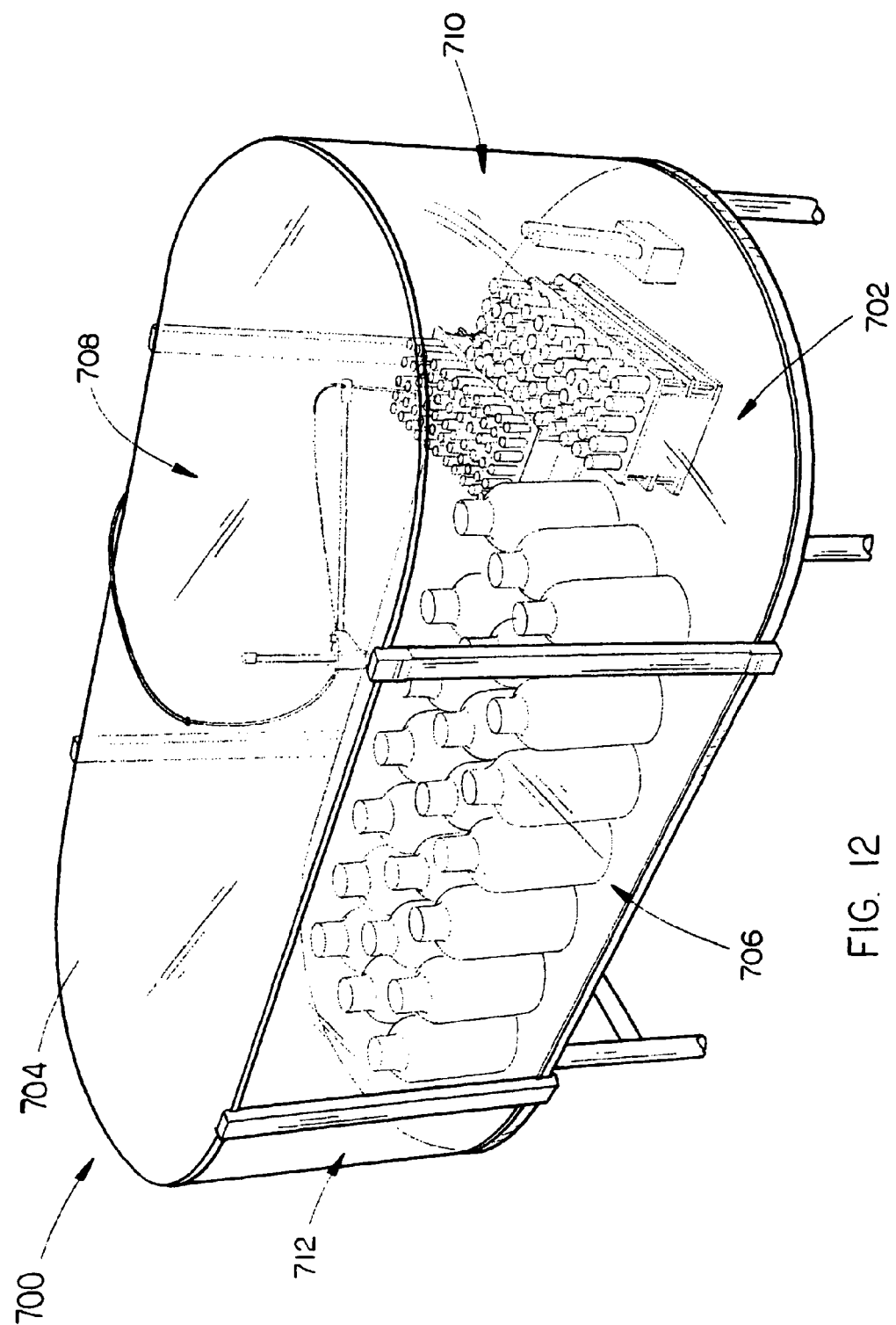
FIG. 12 is an isometric view of an automated sampling or dispensing enclosure in accordance with an exemplary embodiment of the present invention, wherein the enclosure includes two flexible sheets.

Referring specifically to FIG. 12, an enclosure 700 for an automated sampling/dispensing device is provided in which the enclosure 700 surrounds an automated sampling/dispensing device mounted to a circular support surface 702. In an exemplary embodiment, the enclosure 700 includes a lid 704 for covering the support surface 702 on which the automated sampling/dispensing device is mounted. In such embodiment, the lid 704 is generally equivalent in shape and size to that of the support surface 702 allowing the entire support surface 702 to be enclosed and available for use by a user. Further, an aperture for allowing the automated sampling/dispensing device to be connected with devices external to the enclosure may be defined within the lid. As illustrated in FIG. 12, an aperture defined within the lid 704 of the enclosure 700 allows a supply tube to the automated sampling/dispensing device to be connected with an external laboratory analysis equipment. In an alternative embodiment, the enclosure 700 is designed to be airtight allowing the enclosure 700 to contain potentially hazardous chemicals without requiring unnecessary exposure to laboratory personal during sample preparation or analysis.

As illustrated in FIG. 12, the enclosure 700 includes a first support member 706 and a second support member 708. The first 706 and second 708 support members are generally perpendicular to a support surface 702 on which the automated sampling/dispensing device is mounted. For example, as illustrated in FIG. 12, the first support member 706 and the second support member 708 are centered generally one-hundred and eighty degrees opposite from one another. Moreover, such support members may be mechanically coupled to the lid 704 of the enclosure 700 as well as to the support surface 702. For instance, fasteners such as screws, bolts, nuts, and the like may be used to fasten the support members to the lid and support surface. In an advantageous embodiment, all fasteners are either metal-free or coated with an inert plastic coating to prevent interaction of such fasteners with chemical reagents or other substances being used with the automated sampling/dispensing device. In an additional embodiment, an aperture may be formed within one or both of the support members to allow tubes, cords, and the like to be connected to the automated sampling dispensing device contained within the enclosure as well as to external devices (e.g., laboratory analysis equipment), power sources, and the like. It is contemplated that the lid 704 as well as the first support member 706 and the second support member 708 may be formed of inert, light-weight material including Plexiglass® (generically known as the chemical Lucite or polymethyl methacrylate.)

In additional embodiments, as illustrated in FIG. 12, a first flexible sheet 710 and a second flexible sheet 712 are operationally coupled to at least one of the lid 708 or the first support member 706 or the second support member 708. In an embodiment, the first flexible sheet 710 includes a first and second end. The first end of the first flexible sheet 710 includes a finished edge while the second end of the first flexible sheet 710 is fixedly coupled to the second support member 708. For example, the first end of the flexible sheet 710 is finished with a hardened-plastic cover which extends substantially along the length of the first end of the first flexible sheet 710. In addition, at least one guide member is attached to the first end of the first flexible sheet 710 to allow position of the first flexible sheet to be varied.

Figure 13:
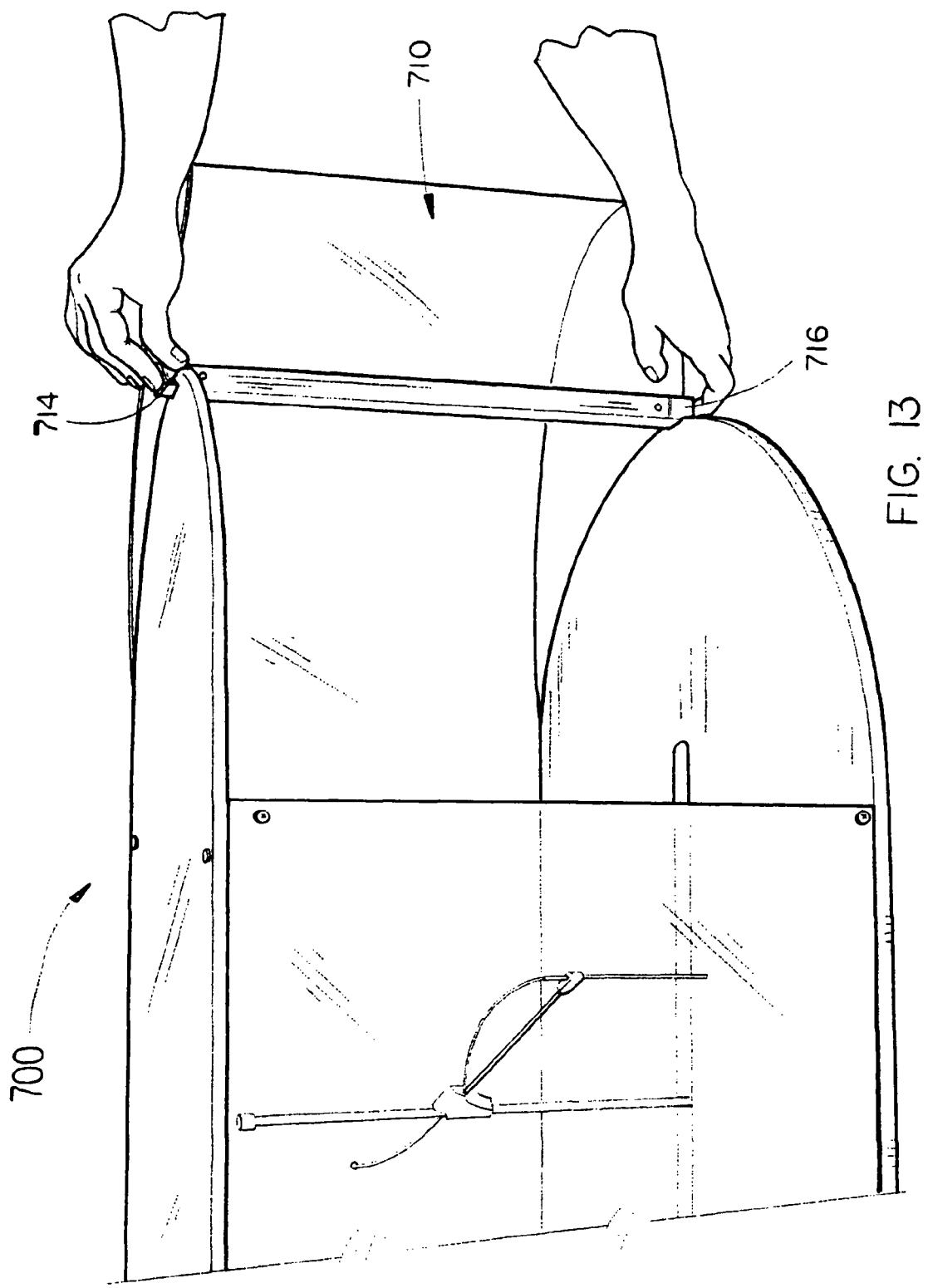
FIG. 13 is a partial front view of the automated sampling or dispensing device enclosure as illustrated in FIG. 12, wherein one of the flexible sheets of the enclosure is retracted.
Figure 14:
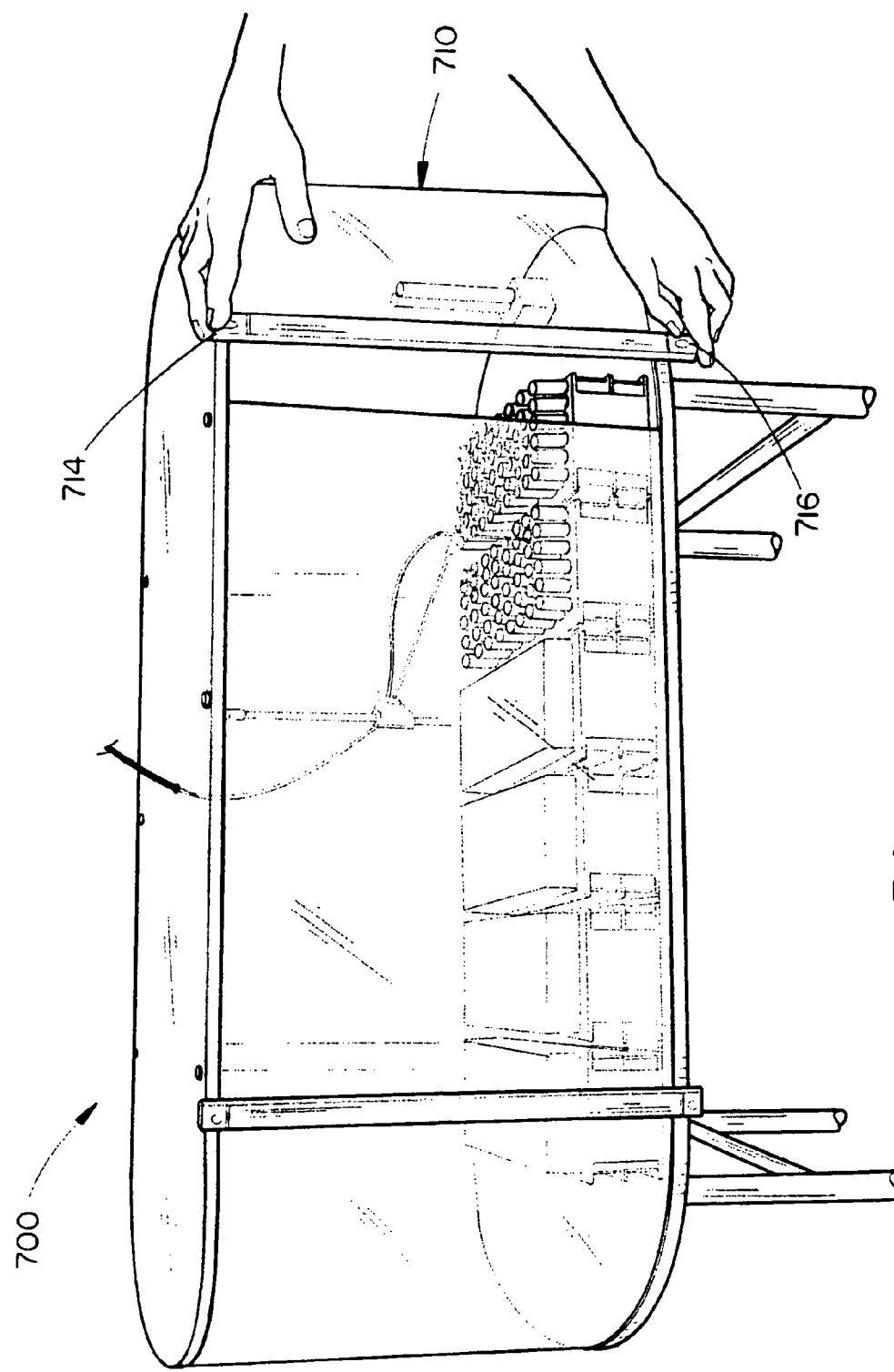
FIG. 14 is a front view of the automated sampling or dispensing device enclosure as illustrated in FIG. 12, wherein the mechanism of fastening a flexible side shut is demonstrated.

As illustrated in FIGS. 13 and 14, the first end of the first flexible sheet 710 includes a first guide member 714 and a second guide member 716 to allow a user to slide the first flexible sheet 710 along an edge of the support surface 702. In an embodiment, the first guide member 714 and the second guide member 716 are press-fit latches allowing a user to secure the flexible sheet at multiple positions along the edge or side of the support surface. For example, a user may release the flexible sheet by applying pressure to the press-fit latches. As illustrated in FIG. 14, a flexible sheet may be moved from a first position to a second position by guiding the first guide member 714 along the edge of the lid 704 while the second guide member is detached from the support surface 710. It is contemplated that additional mechanisms may be employed to guide and secure the flexible sheet at various positions, including fasteners such as clips, pressure-sensitive screws, and the like. It is further contemplated that a channel may be formed within the support surface to provide an area in which a guide member may slide and ultimately, be secured.

In the present embodiment, the second flexible side 712 includes a first and second end. The first end of the second flexible sheet 712 includes a finished edge while the second end of the second flexible sheet 712 is fixedly coupled to the second support member 708. For example, the first end of the second flexible sheet 712 is finished with a hardened-plastic (e.g., plexi-glass) cover which extends substantially along the length of the first end of the second flexible sheet 712. In addition, at least one guide member is attached to the first end of the second flexible sheet 712 to allow position of the first flexible sheet to be varied. For instance, the first end of the second flexible sheet 712 may include a first guide member 714 and a second guide member 716 to allow a user to slide the second flexible sheet 712 along an edge or side of the support surface 702. In an embodiment, the first guide member 714 and the second guide member 716 are press-fit latches allowing a user to secure the flexible sheet at multiple positions along the edge or side of the support surface. It is contemplated that additional mechanisms may be employed to guide and secure the flexible sheet at various positions, including fasteners such as clips, pressure-sensitive screws, and the like.

Figure 15:
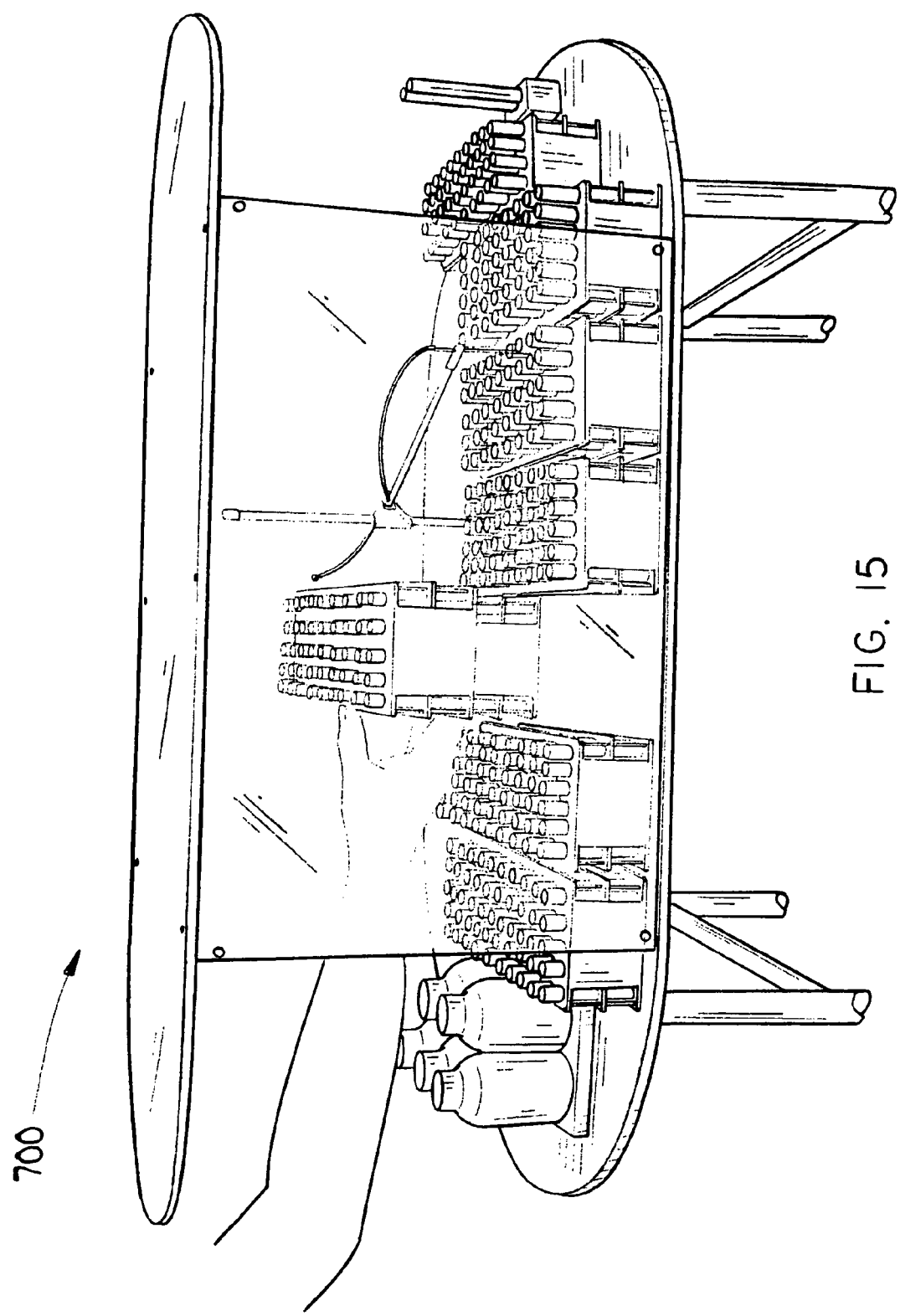
FIG. 15 is a front view of the automated sampling or dispensing device enclosure as illustrated in FIG. 12, wherein the flexible sheets have been removed.

Referring to FIG. 15, the first and second flexible sheets have been removed to allow efficient access to the support surface 702. In an embodiment, the first and second flexible sheets are detachable. The detachable features of such sheets allows a user to load or remove samples efficiently from the support surface 702 in which a user does not have to reposition the sheets in order to gain access to a specific support surface area. It is contemplated that one or both sheets may be removed depending upon the needs of the user.

Figure 16:
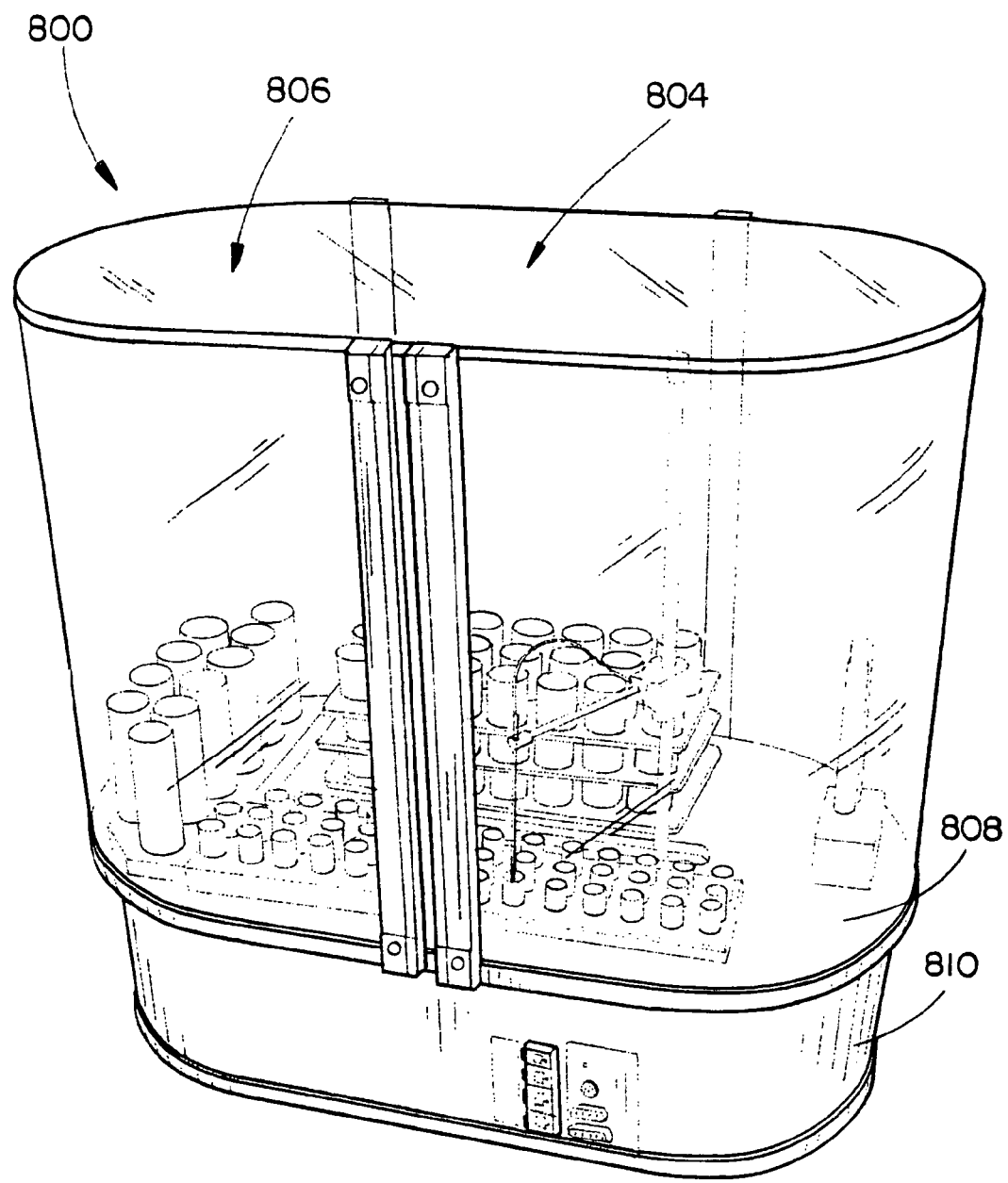
FIG. 16 is an isometric view an enclosure for a bench top automated sampling or dispensing device in accordance with an exemplary embodiment of the present invention, wherein the enclosure includes flexible sheets which are in a closed position.
Figure 17:
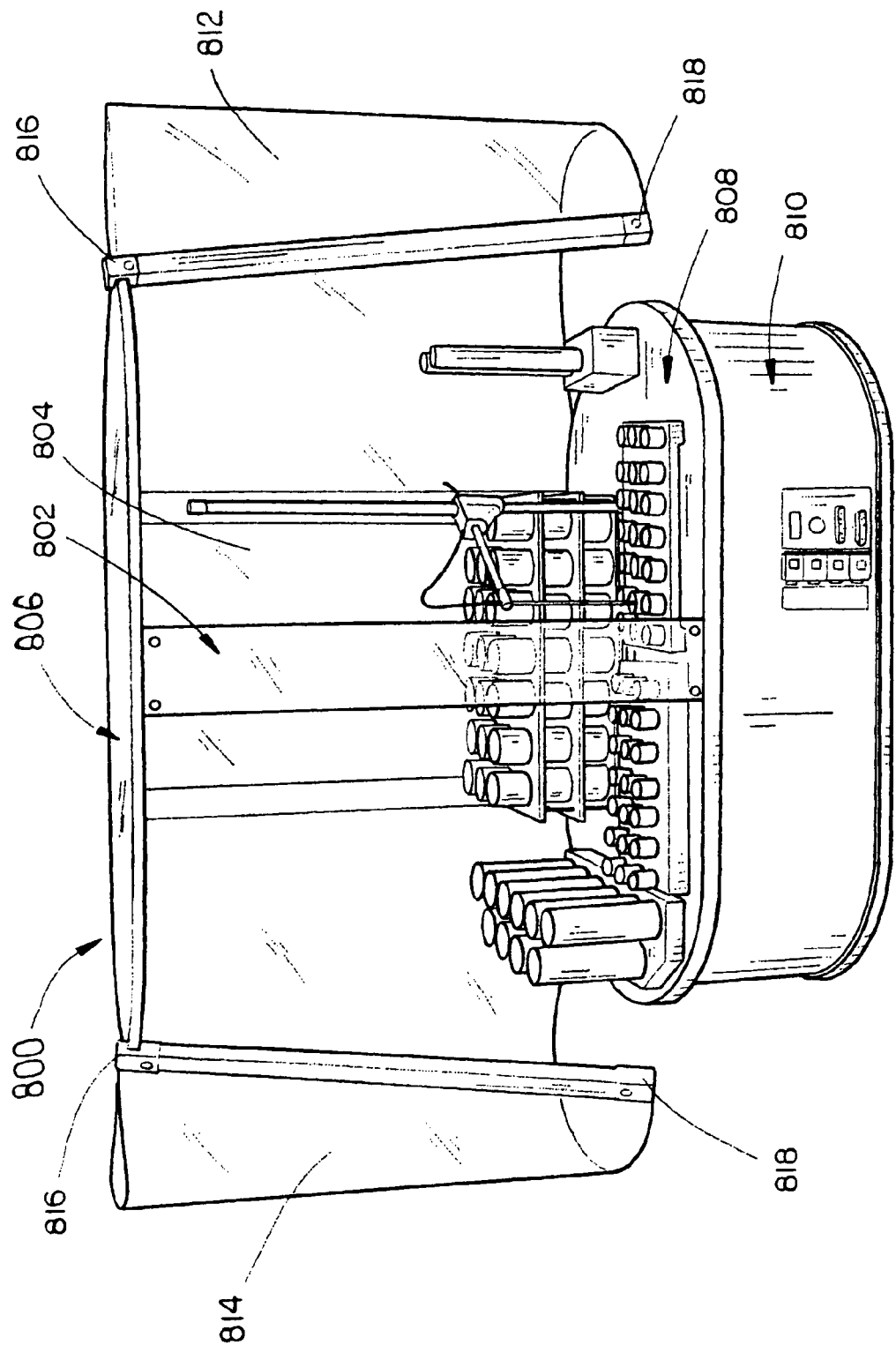
FIG. 17 is a front view of the enclosure for the bench top automated sampling or dispensing device as illustrated in FIG. 16, wherein the flexible sheets are in an open position.

Referring to FIGS. 16 and 17, an additional exemplary enclosure for enclosing an automated sampling/dispensing device is provided in which the automated sampling/dispensing device is a bench-top automated sampling dispensing device. As illustrated in FIGS. 16 and 17, an enclosure 800 for a bench-top automated sampling dispensing device is configured in a similar manner as the enclosure 700 for a table-top automated sampling/dispensing device. The enclosure 800 includes a first support member 802 and a second support member 804 for supporting a lid 806. In an exemplary embodiment, the lid 806 covers a support surface 808 secured to a base 810 of the bench-top automated sampling/dispensing device. In such embodiment, the lid 806 is generally equivalent in shape and size to that of the support surface 808 allowing the entire support surface 808 to be enclosed and available for use by a user. Further, the first 802 and second 804 support members are generally perpendicular to the support surface 808.

As illustrated in FIGS. 16 and 17, the first support member 802 and the second support member 804 are centered generally one-hundred and eighty degrees opposite from one another. For example, the first support member 802 is positioned on the front-side of the automated sampling/dispensing device (the front side being defined as the side including a user power control panel) while the second support member 804 is positioned generally opposite the first support member 802 (e.g., to the rear-side of the automated sampling/dispensing device). Moreover, such support members may be mechanically coupled to the lid 806 of the enclosure 800 as well as to the support surface 808. For instance, fasteners such as screws, bolts, nuts, and the like may be used to fasten the support members to the lid and support surface. In an advantageous embodiment, all fasteners are either metal-free or coated with an inert plastic coating to prevent interaction of such fasteners with chemical reagents or other substances being used with the automated sampling/dispensing device.

It is contemplated that the lid 806 as well as the first support member 802 and the second support member 804 may be formed of inert, light-weight material including Plexiglass® (generically known as the chemical Lucite or polymethyl methacrylate). It is further contemplated that the enclosure 800 may include an aperture within the lid or at least one of the support members allowing for the automated sampling/dispensing device to be connected with devices external to the enclosure. For example, an aperture may be defined within the lid for allowing a supply tube to the automated sampling/dispensing device to be connected with external laboratory analysis equipment. In an alternative embodiment, the enclosure 800 is designed to be airtight allowing the enclosure to contain potentially harmful chemicals without requiring unnecessary exposure to laboratory personal during sample preparation or analysis.

In additional exemplary embodiments, as illustrated in FIG. 17, a first flexible sheet 812 and a second flexible sheet 814 are operationally coupled to at least one of the lid 806 or the first support member 802 or the second support member 804. In an embodiment, each flexible sheet includes a first and second end. The first end of each flexible sheet includes a finished edge while the second end of each flexible sheet is fixedly coupled to the second support member 804. For example, the first end of the flexible sheet 812 is finished with a hardened-plastic cover (e.g., Plexiglass®) which extends substantially along the length of the first end of the first flexible sheet 812.

In further exemplary embodiments, at least one guide member is attached to the first end of each flexible sheet to allow the position of each flexible sheet to be varied. As illustrated in FIG. 17, the first end of each flexible sheet includes a first guide member 816 and a second guide member 818 to allow a user to slide each sheet along an edge of the lid 806 or support surface 808. In an embodiment, the first guide member 816 and the second guide member 818 are press-fit latches allowing a user to secure the flexible sheet at multiple positions along the edge or side of the lid or support surface. For example, a user may release the flexible sheet by applying pressure to the press-fit latches. As illustrated in FIG. 17, a flexible sheet may be moved from a first position to a second position by guiding the first guide member 816 along the edge of the lid 806 while the second guide member 818 is detached from the support surface 808. It is contemplated that additional mechanisms may be employed to guide and secure the flexible sheet at various positions, including fasteners such as clips, pressure-sensitive screws, and the like. It is further contemplated that a channel may be formed within the support surface to provide an area in which a guide member may slide and ultimately, be secured.

It is contemplated that the first and second flexible sheets may be detachable. The detachable features of such sheets allows a user to load or remove samples efficiently from the support surface 808 in which a user does not have to reposition the sheets in order to gain access to a specific support surface area. It is contemplated that one or both sheets may be removed depending upon the needs of the user.

Figure 18:
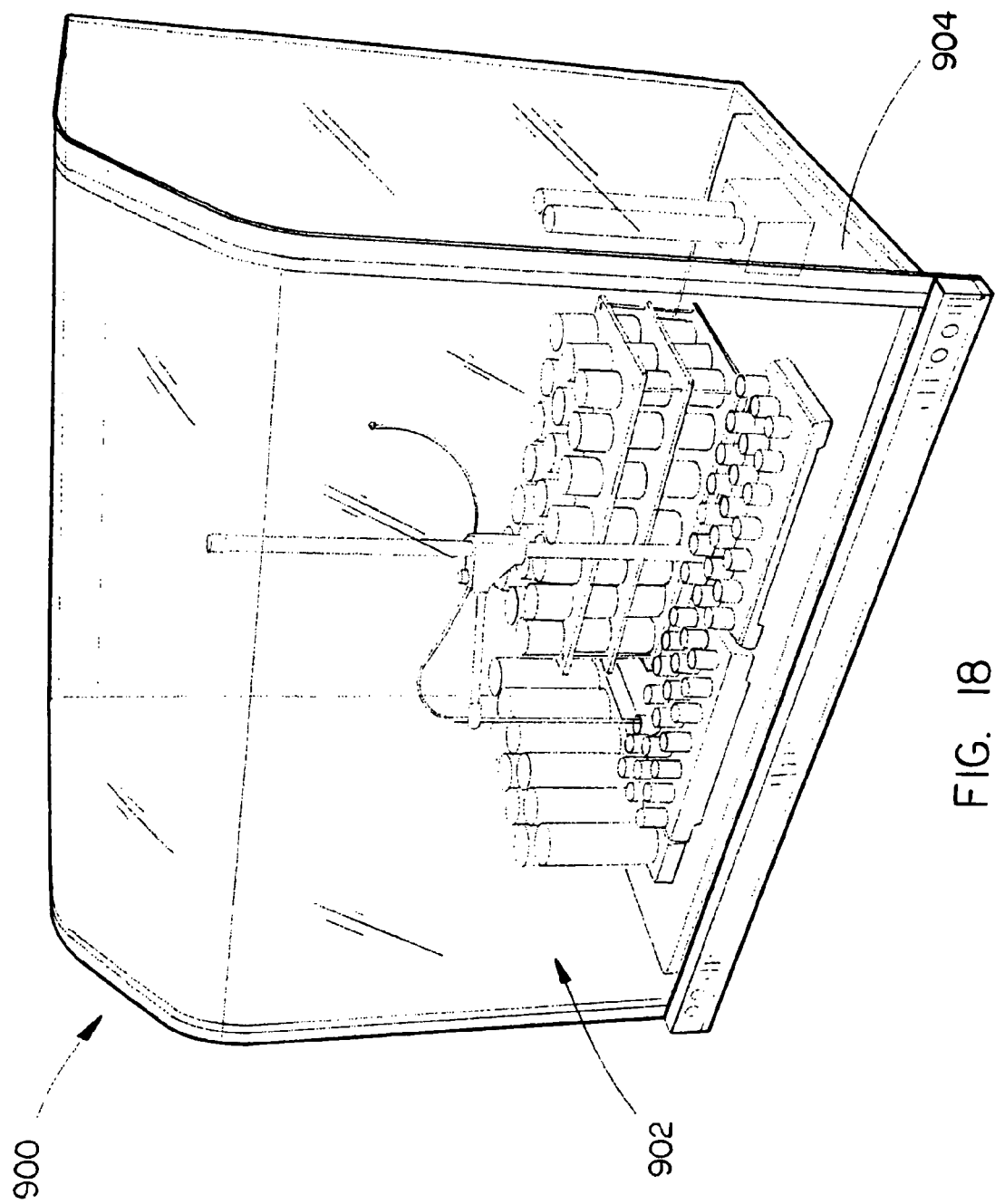
FIG. 18 is an isometric view of an enclosure for an automated sampling or dispensing device in accordance with an additional exemplary embodiment of the present invention, wherein the enclosure includes a single flexible front sheet.
Figure 19:
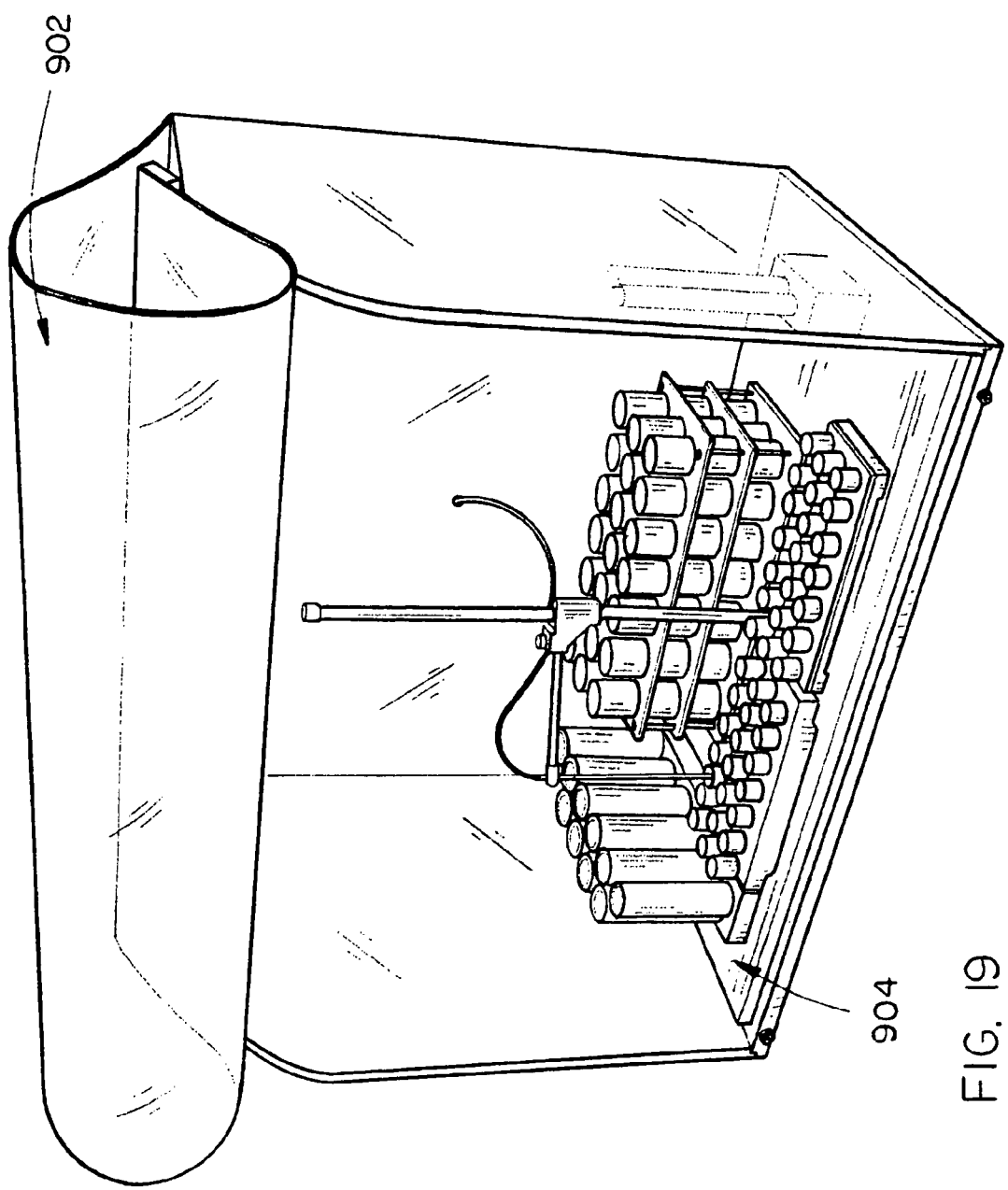
FIG. 19 is an isometric view of the enclosure for the automated sampling or dispensing device as illustrated in FIG. 18, wherein the front sheet is retracted allowing access to the device.

Referring to FIGS. 18 and 19, a further exemplary enclosure 900 for enclosing an automated sampling/dispensing device is provided in which the enclosure 900 includes a single flexible sheet or panel 902. As illustrated in FIGS. 18 and 19, the enclosure 900 includes a plurality of support walls and a single flexible sheet 902 for enclosing the automated sampling/dispensing device mounted on a support surface 904. For example, the enclosure 900 may include three support walls and the single flexible sheet 902. In such example, a first side support wall and a second side support wall provide support to a rear support wall in which the rear support wall is secured to an edge of the first side support wall and an edge of the second side support wall. The rear support wall is generally opposite to that of the front of the enclosure. Further, the front of the enclosure being that which includes the flexible sheet and is utilized by a user to gain access to the automated sampling/dispensing device. The first and second side support walls are configured to allow the flexible sheet to be rolled along an outer edge of the first side support wall and an outer edge of the second side support wall. It is contemplated that an aperture may be defined within at least one of the plurality of walls for allowing the enclosed apparatus to be connected with external devices or power sources.

With continued reference to FIGS. 18 and 19, the single flexible sheet 902 includes a first and second edge. The first end of the flexible sheet 902 includes a finished edge while the second end of the flexible sheet 902 is fixedly coupled to the rear support wall. For example, the first end of the flexible sheet 902 is finished with a hardened-plastic cover which extends substantially along the length of the first end of the flexible sheet 902. To gain access to the interior of the enclosure 900, the single flexible sheet 902 may be retracted with a first end of the first edge of the single flexible sheet 902 being secured to the outer edge of the first side support wall and a second end of the first edge being secured to the outer edge of the second side support wall. It is contemplated that various mechanisms may be employed to secure the first edge of the flexible sheet 902 to the side support edges including press fit latches, clips, screws, and the like. In addition, the enclosure 900 may be mounted to an automated sampling/dispensing device which is integral to laboratory analysis equipment in which the enclosure may positioned to enclose such device by securing the enclosure to a support area supporting the device. Moreover, the single flexible sheet may be detachable allowing a user access to the entire support surface area as well as to the over-head support surface area.

Although the presently disclosed enclosure focuses upon the use of such enclosure with an automated sampling/dispensing device, it is contemplated that such enclosure may be employed with a variety of types of laboratory equipment without departing from the scope and spirit of the present invention. It is further contemplated that the aforementioned exemplary enclosures may be ventilated with may be ventilated to prevent the entry of contaminates such as bacteria or air-borne substances into the external environment. For instance, the air drawn into the enclosure is passed through a HEPA filter.

Figure 20:
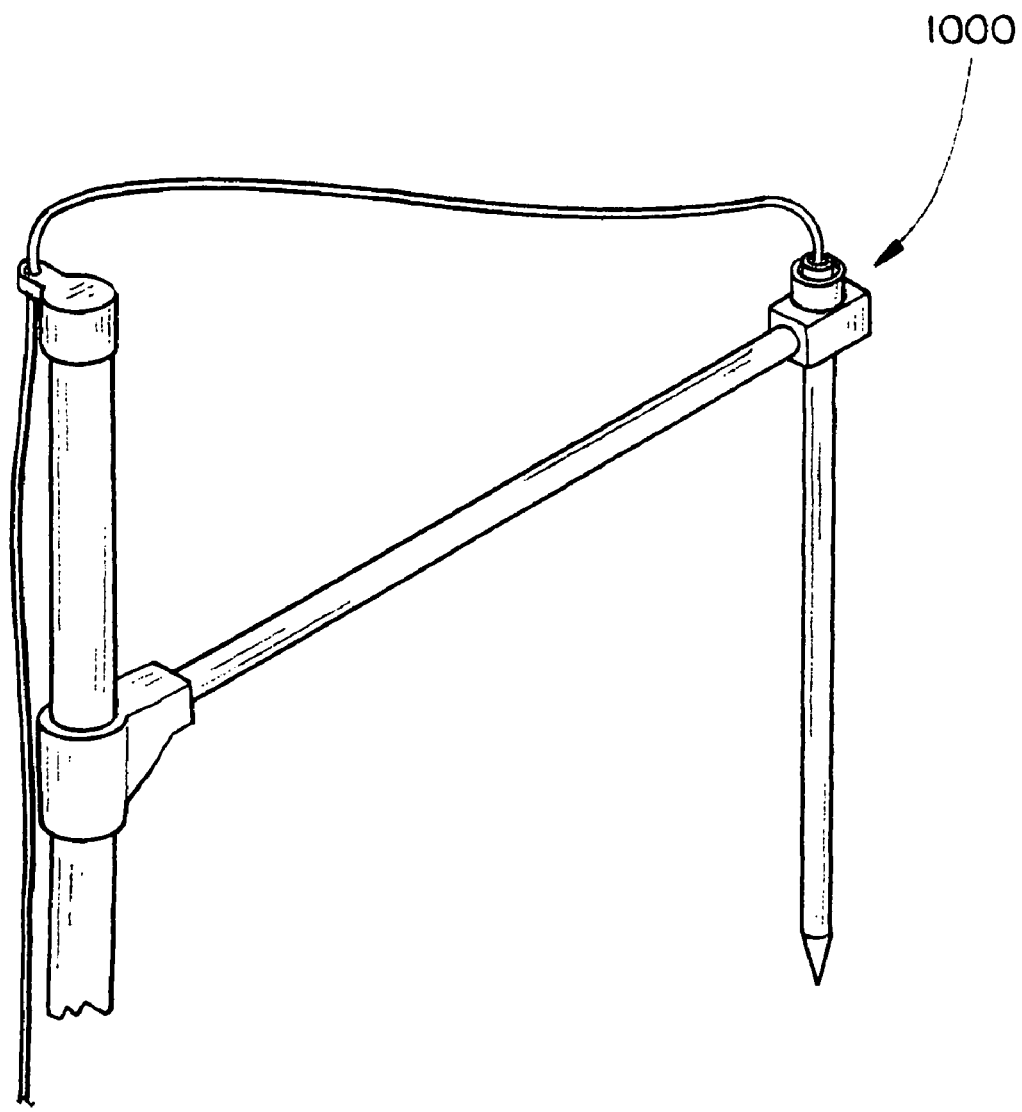
FIG. 20 is a partial isometric view of a sample arm assembly for an automated sampling or dispensing device in accordance with an exemplary embodiment of the present invention, wherein the sample arm assembly includes a dampening device for dampening vibrations generated during use.

Referring now to FIG. 20, a sample arm assembly for an automated sampling or dispensing device in accordance with an exemplary embodiment of the present invention is provided in which the sample arm assembly includes a dampening device for dampening vibrations generated during use. As illustrated in FIG. 20, the sample arm assembly includes the sample probe 114 allowing samples to be dispensed or removed from various sample vessels. A dampening device 1000 is positioned around a first end of the sample probe 114 which is generally opposite to a second end of the sample probe 114, the second end of the sample probe making contact with sample and sample vessels. The dampening device 1000 allows the vibrations generated during operation of the automated sampling/dispensing device to be minimized by moving out of phase with the automated sampling/dispensing device sample probe. The minimization of the vibrations allows accurate positioning of the sample probe and thus, minimizes the possibility of sample cross-contamination without requiring the speed of the automated sampling/dispensing device to be reduced.

Figure 21:
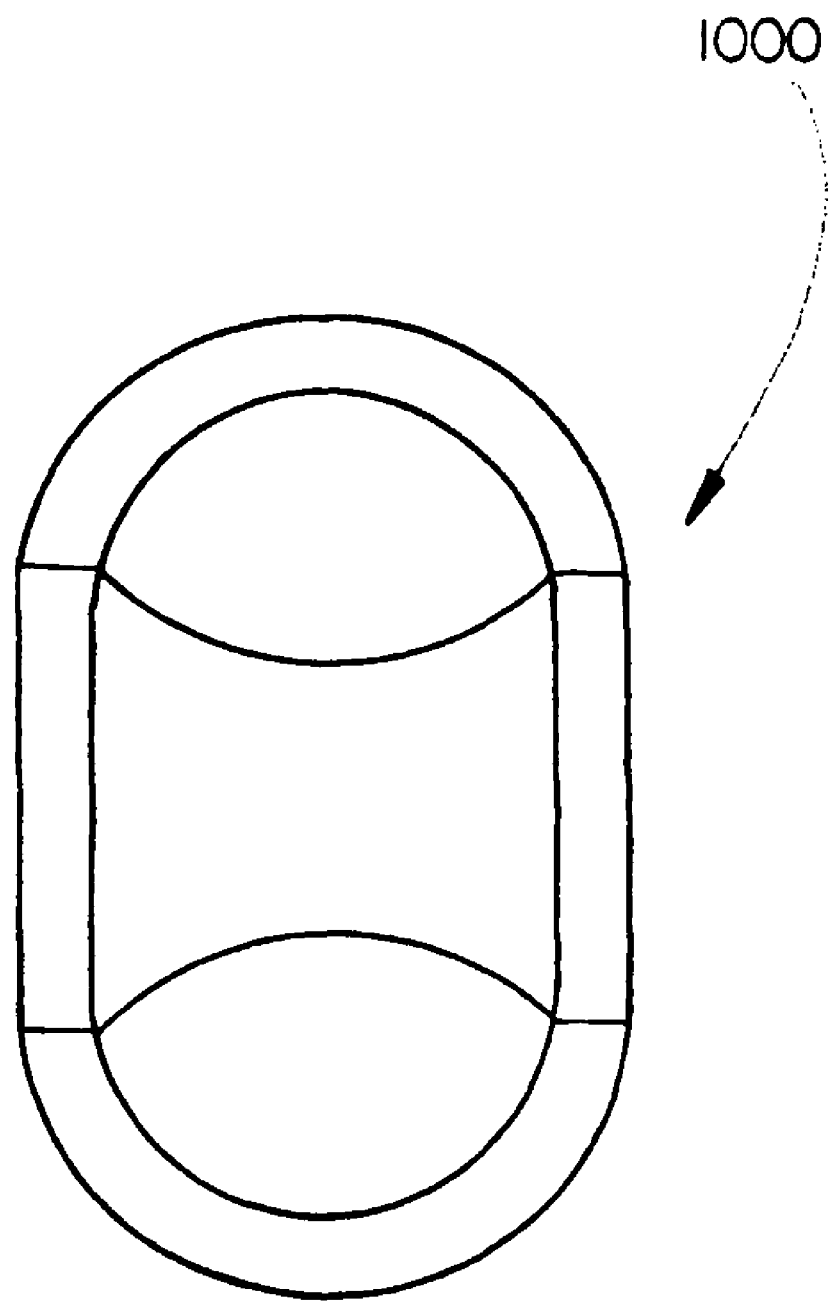
FIG. 21 is an isometric view of a dampening device for an automated sampling or dispensing device in accordance with an exemplary embodiment of the present invention.

In an exemplary embodiment, the dampening device 1000 includes a body 1002 with a plurality of walls. As illustrated in FIG. 21, the body 1002 is generally cylindrical and includes a first end and a second end. Further, a first opening 1004 is defined within the first end and a second opening 1006 is defined within the second end. Further, in an embodiment, the body 1002 includes an inner diameter greater than an outer diameter of an automated sampling/dispensing device sample probe. For example, for a sample probe with a diameter of 3 millimeters, the inner diameter of the cylindrical body is approximately 6 millimeters. The use of a dampening device with an inner cylindrical diameter approximately two times that of the sample probe allows the device to be placed loosely around the first end of the sample probe. During operation, the dampening device is allowed to move out of phase with the automated sampling/dispensing device sample probe allowing sample probe vibrations to be dampened.

Figure 22B:
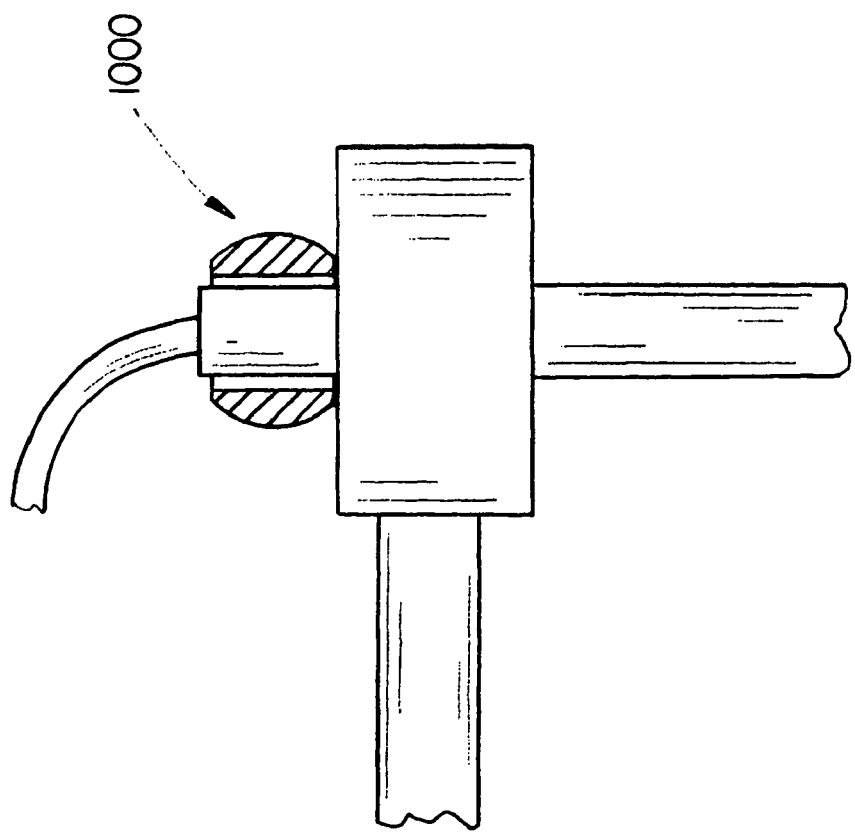
FIG. 22B is a partial side view of an automated sampling or dispensing device in accordance with an exemplary embodiment of the present invention, wherein a cross-sectional view of an additional exemplary dampening device.
Figure 22A:
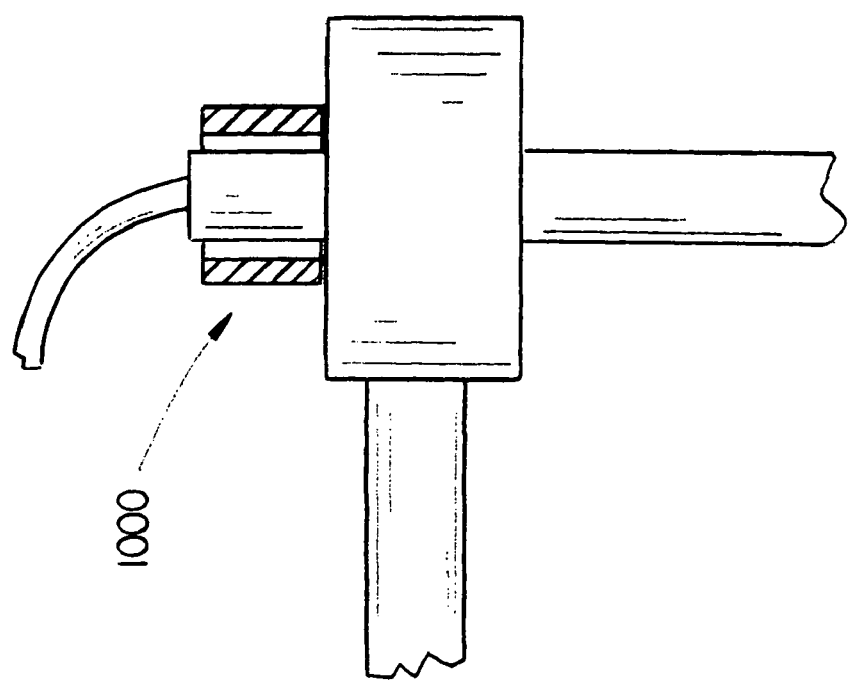
FIG. 22A is a partial side view of an automated sampling or dispensing device in accordance with an exemplary embodiment of the present invention, wherein a cross-sectional view of an exemplary dampening device.

It is contemplated that the dampening device may be composed of metal-free, inert material including plastic. The use of metal-free, inert materials allows the dampening device to be lightweight and removes the possibility of the device reacting with any chemicals or other substance. It is further contemplated that the size and shape of the dampening device may vary depending upon the size and shape of the sample probe on which it is to be positioned. For example, as illustrated in FIGS. 22A and 22B, the inner diameter of the dampening device may be square or spherical, respectively.

In an additional exemplary embodiment, the body 1002 of the dampening device 1000 includes a slit extending along the length of the cylindrical body for allowing the dampening device 1000 to be positioned around the first end of the sample probe 114 which is generally opposite to the second end of the sample probe 114 which makes contact with a sample. The slit allows the dampening device 1000 to be positioned without requiring the user to slide the device over additional components of the automated sampling/dispensing device. For example, the slit is of a width to allow the dampening device 1000 to be positioned around the first end of the sample probe 114 and remain around the first end of the sample probe 114 during sample probe operation.

Figure 23:
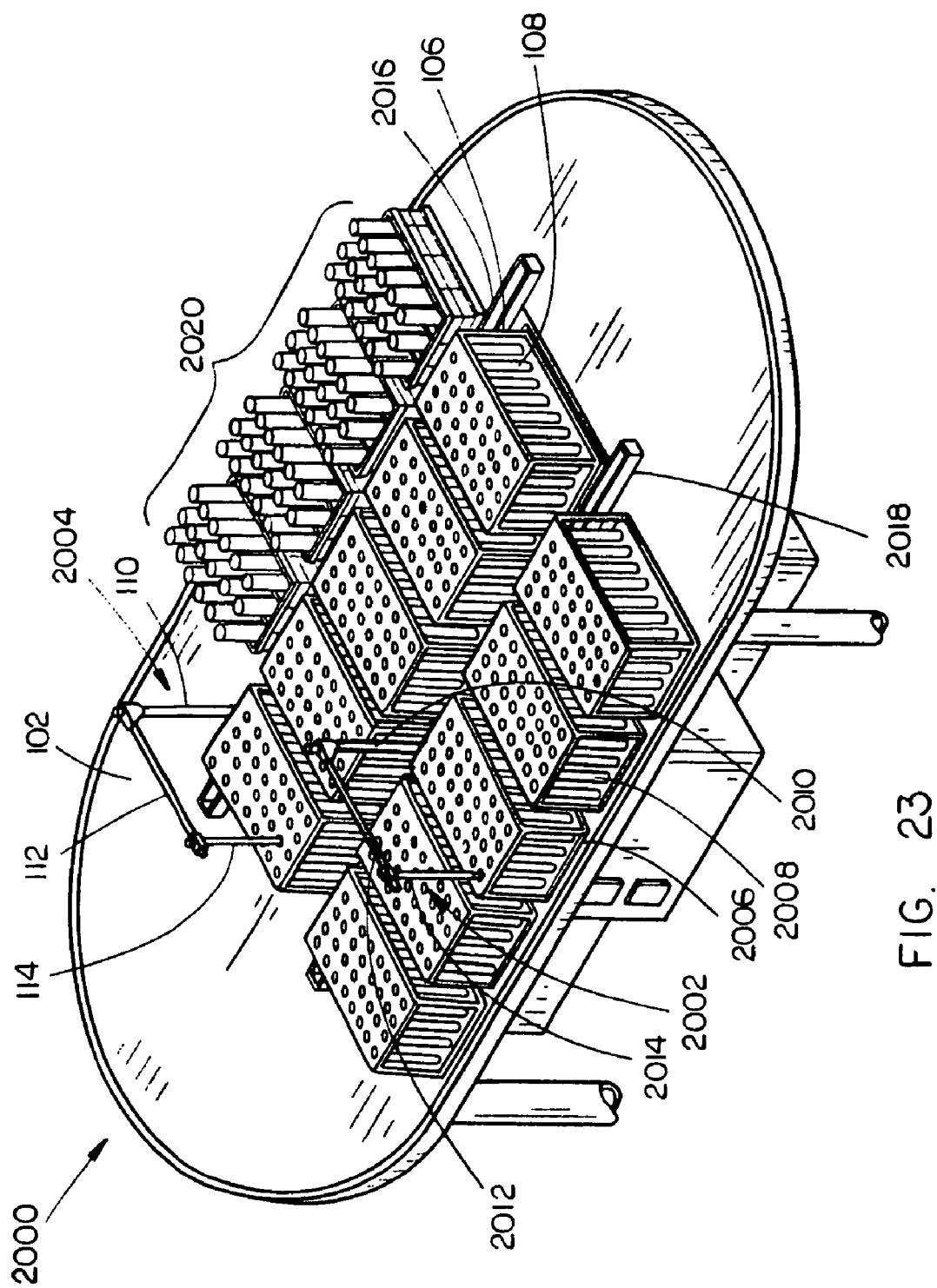
FIG. 23 is an isometric view of a dual arm automated sampling or dispensing device in accordance with an exemplary embodiment of the present invention.
Figure 24:
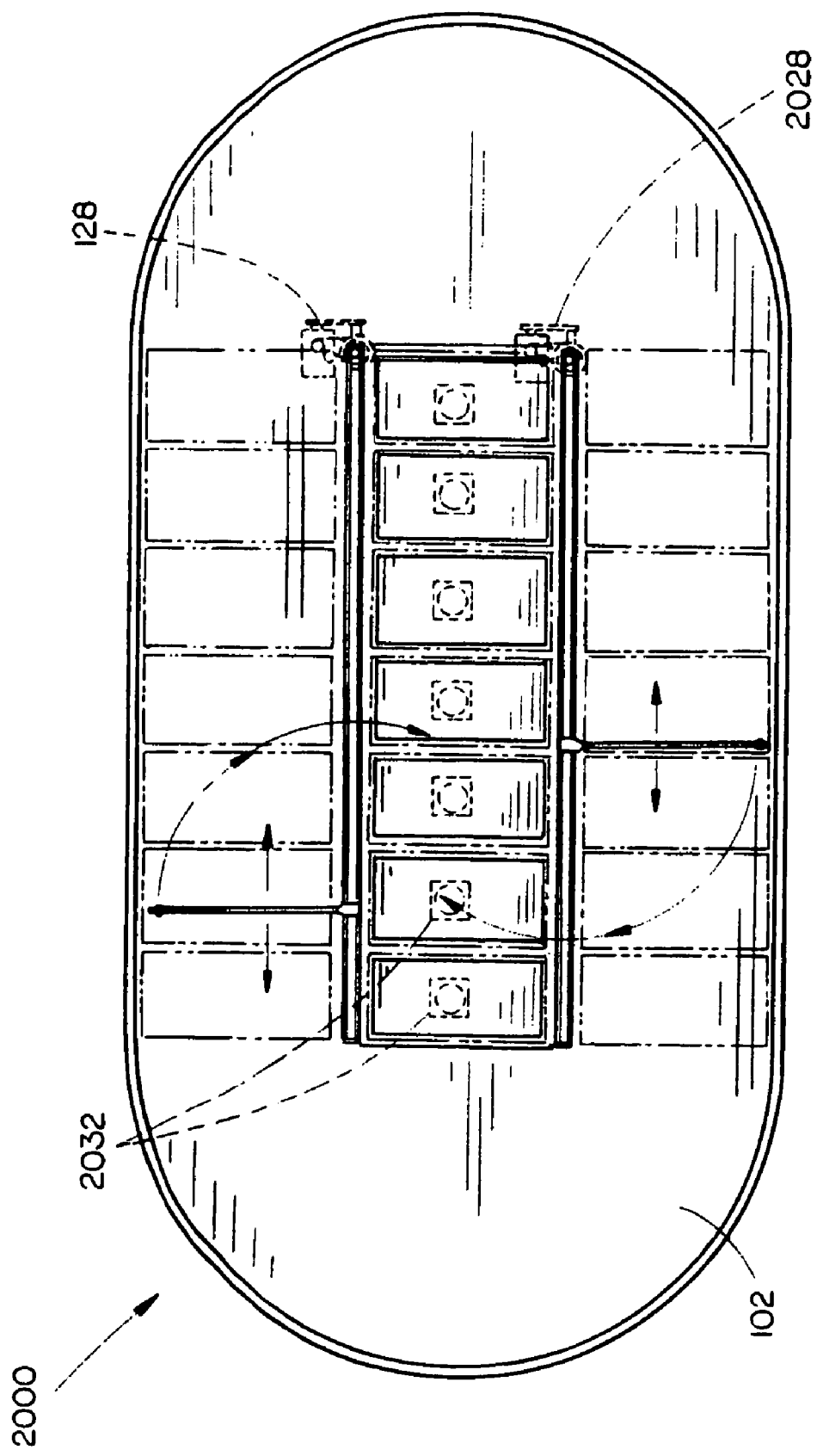
FIG. 24 is a top view of a dual arm automated sampling or dispensing device in accordance with an exemplary embodiment of the present invention.
Figure 25:
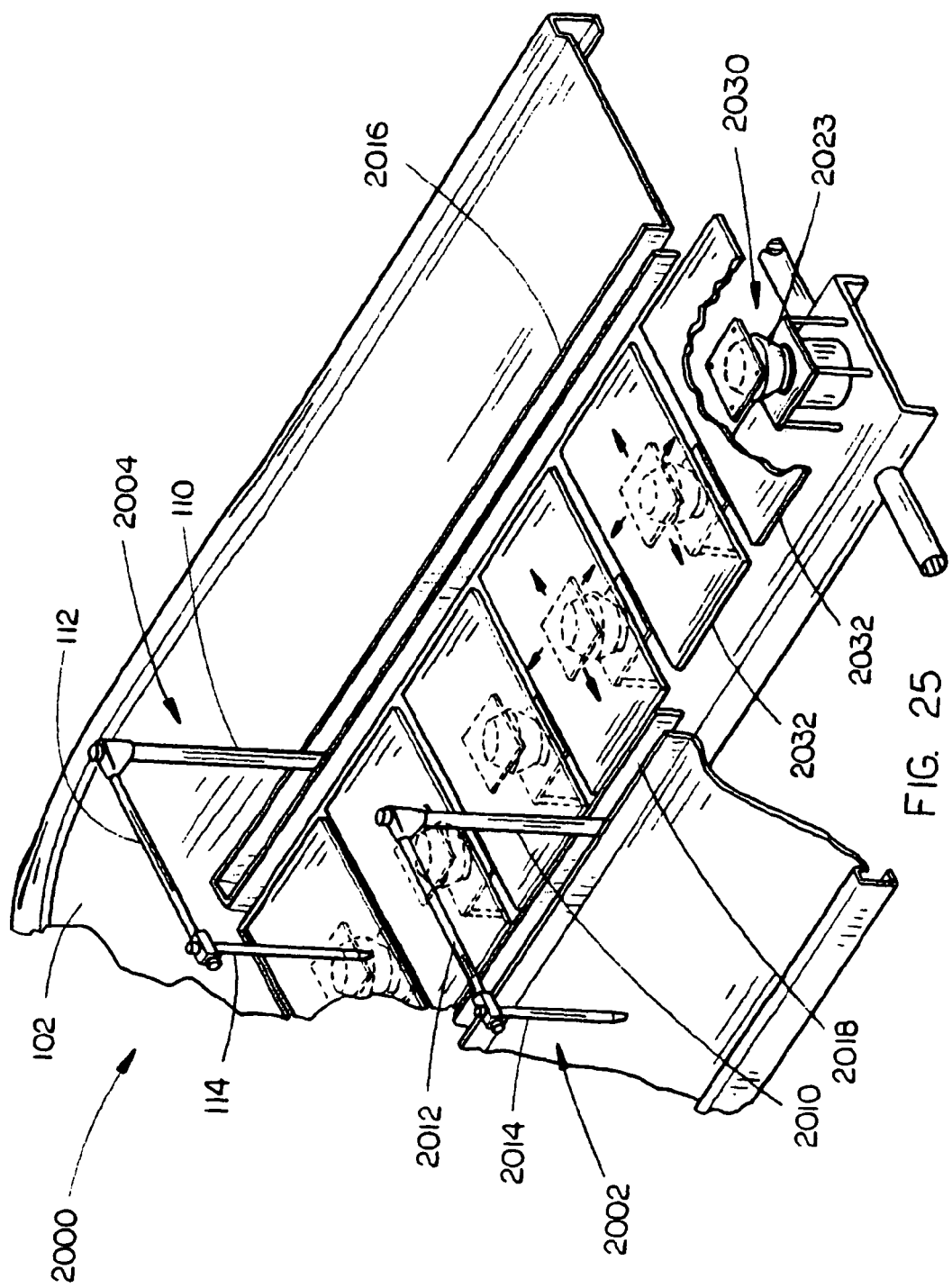
FIG. 25 is an exploded view of a mixing assembly of a dual arm automated sampling or dispensing device in accordance with an exemplary embodiment of the present invention.
Figure 26:
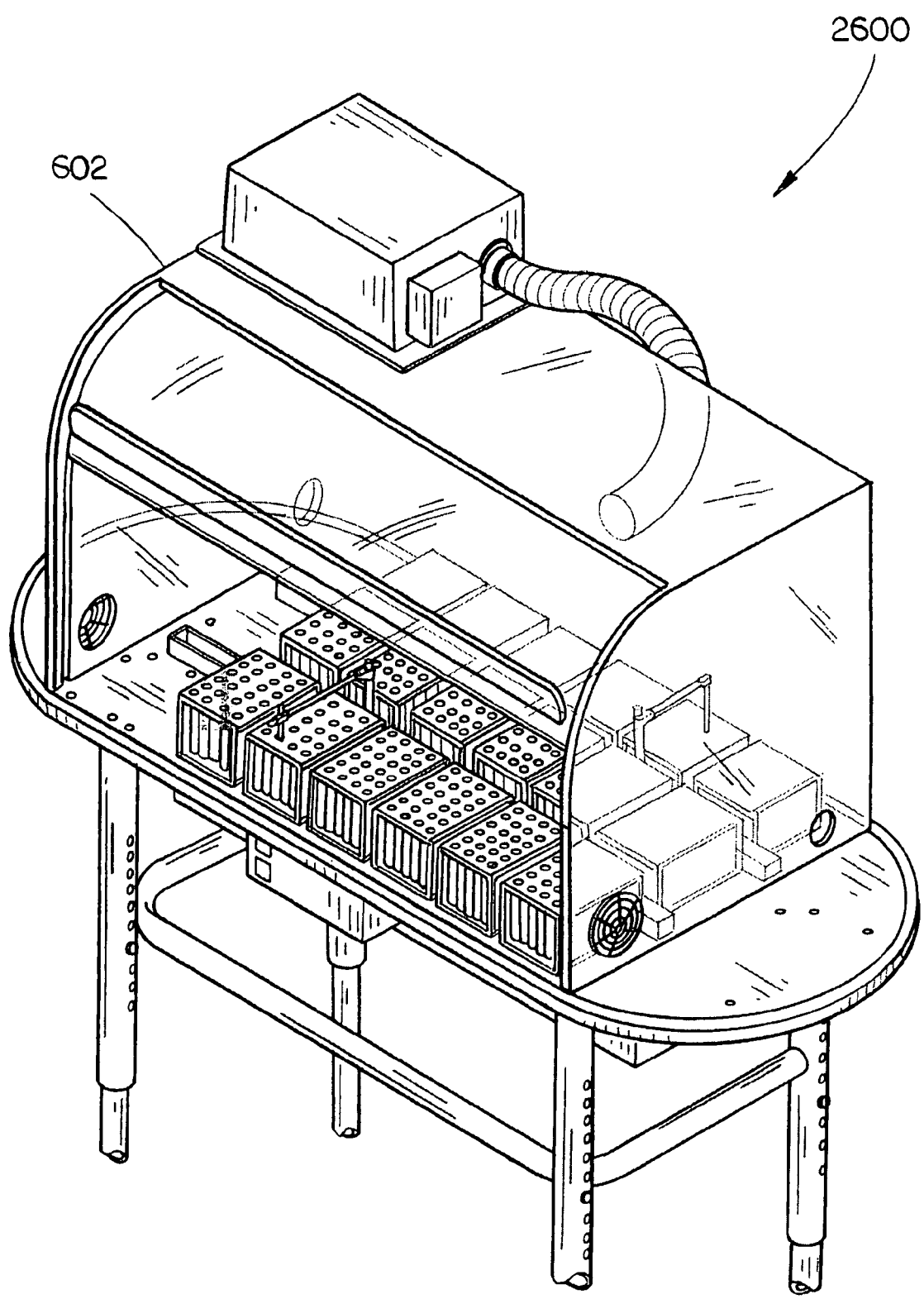
FIG. 26 is an isometric view of a dual arm automated sampling or dispensing device in an enclosure in accordance with an exemplary embodiment of the present invention.
Figure 27:
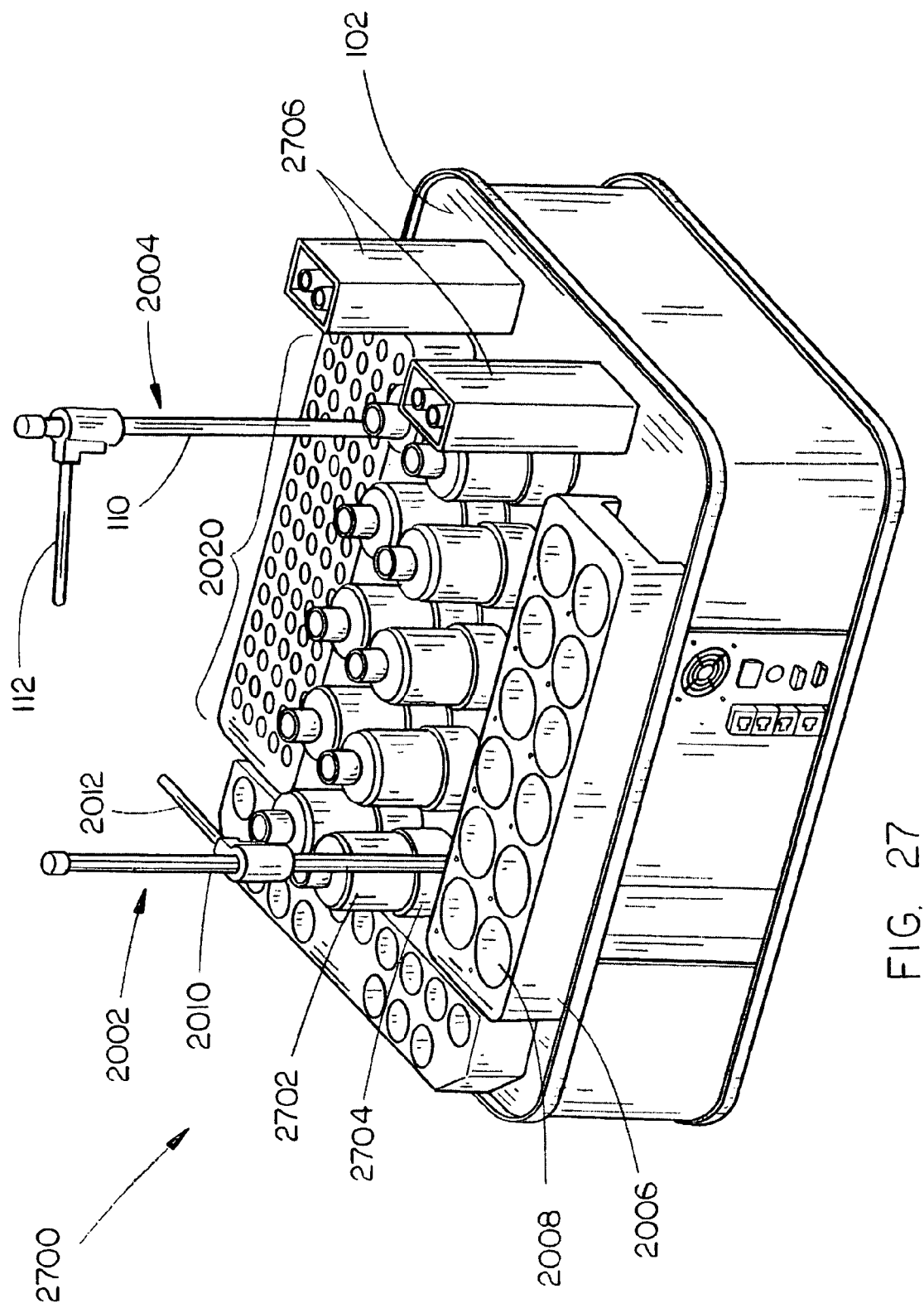
FIG. 27 is an isometric view of a dual arm automated sampling or dispensing device in an in accordance with an exemplary embodiment of the present invention.
Figure 28:
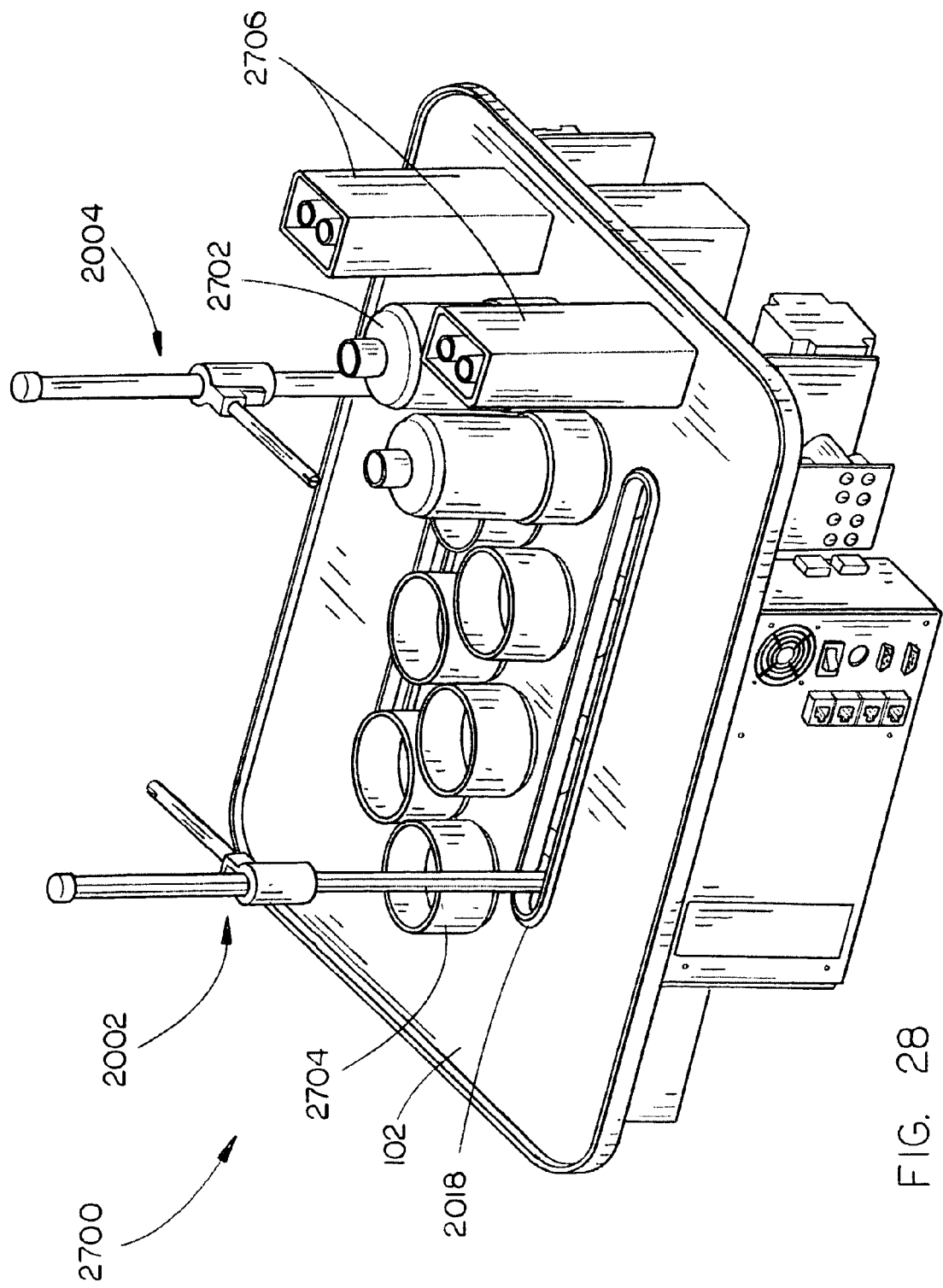
FIG. 28 is an isometric view of a dual arm automated sampling or dispensing device in an in accordance with an exemplary embodiment of the present invention.

Referring to FIGS. 23-26 generally, a dual arm automated sampling or dispensing device 2000 in accordance with an exemplary embodiment of the present invention is shown. Specifically, FIG. 23 is an isometric view of a dual arm automated sampling or dispensing device in accordance with an exemplary embodiment of the present invention. FIG. 24 is a top view of a dual arm automated sampling or dispensing device in accordance with an exemplary embodiment of the present invention. FIG. 25 is an exploded view of a mixing assembly of a dual arm automated sampling or dispensing device in accordance with an exemplary embodiment of the present invention and FIG. 26 is an isometric view of a dual arm automated sampling or dispensing device in an enclosure in accordance with an exemplary embodiment of the present invention.

In the embodiment described in FIGS. 23-26, automated sampling or dispensing device 2000 may comprise a first arm assembly 2002 suitable for collecting an amount of a fluid from a fluid holder and adding the collected fluid to a sample vessel holding an amount of sample, a second arm assembly 2004 suitable for collecting an amount of sample or sample and fluid from a sample vessel and depositing the collected sample or fluid and sample mixture to a vessel or container 2020 suitable for transfer to an analyzer for analysis, or directly to an analyzer for analysis.

Automated sampling or dispensing device 2000 may comprise a support surface 102 for supporting a sample holder 106 and a fluid holder 2006, the sample holder 106 being suitable for holding a sample vessel 108, and the fluid holder 2006 being suitable for holding a fluid vessel 2008, a first arm assembly 2002 comprising a z-axis support 2010 and a fluid probe support arm 2012 that supports a fluid probe 2014, and a first drive assembly 2028 coupled to the z-axis support of the sample arm assembly for powering and positioning the first arm assembly 2002. Device may further comprise a second arm assembly 2004 for supporting a sample probe 114. The second arm assembly 2004 comprises a z-axis support 110 and a horizontal support arm 112, and a second drive assembly 128 coupled to the z-axis support of the second arm assembly 2004 for powering and positioning the second arm assembly. The first drive assembly causes the first arm assembly to move in translation along the x-axis, in translation along an axis coaxial with the z-axis support, and radially about the z-axis. The second drive assembly causes the second arm assembly to move in translation along the x-axis, in translation along an axis coaxial with the z-axis support, and radially about the z-axis. The first arm assembly is suitable for collecting an amount of fluid from a fluid container and transferring it to a container holding an amount of sample. Transfer may be accomplished by releasing the amount of fluid into the sample vessel prior to transfer of some of or the entire sample to a remote location for analysis. The second arm assembly is suitable for collecting an amount of sample from the sample holder and transferring the collected sample and fluid to an analyzer.

Fluid may be a diluent, an internal standard, a spike, or any other fluid suitable for mixing with a sample prepared for analysis. A diluent may be defined as any liquid or solid material used to dilute or carry an active ingredient. An internal standard may refer to a compound added to each analysis that is used in analyte quantitation. An internal standard may be utilized to verify instrument response and retention time stability. Additionally, an internal standard may be added to a sample extract just before instrumental analysis to permit correction for inefficiencies. A spike may refer to a form of a chemical element having one or more isotope abundance artificially enhanced compared with the natural element.

The technique of standard additions may be utilized when the matrix is quite variable, if internal standard that corrects for plasma related effects is not available, or like circumstances. Standard addition may also be utilized to confirm the ability of an internal standard calibration curve technique to correct for both nebulizer and plasma related effects. The fluid probe may be suitable for splitting the analytical sample solution accurately. For instance if the final sample solution is made to 100.00 grams, 50.00 grams of the sample solution may be transferred to a separate clean container for spiking. The technique of standard additions requires a linear response. It is therefore important to work within the linear working range for each analyte. An analysis of the unknown to estimate analyte levels may be performed to enable an analyst to spike the unknown solution with a concentrate of the analyte(s) of interest to an appropriate level. For instance, an analyte may be spike to levels of between 2x and 3x where x represents the unknown concentration of the analyte of interest.

For ICP, an additional concern is drift. To make an accurate measurement, the automated sampling or dispensing device 2000 may perform multiple spiked additions as necessary. The automated sampling or dispensing device may also enable measurement of the sample along with a single spiked sample several times to account for drift. For instance, a measurement sequence may be blank, sample, blank, spiked sample, blank, sample, blank, spiked sample, and so on, where an average of all measurements may be calculated for the final calculation.

In an exemplary embodiment, the support surface comprises a table. The table of the support surface 102 is comprised of a first slot 20 and a second slot. The first arm assembly is attached to the first drive assembly by the z-axis support extending through the first slot, and the second arm assembly is attached to the second drive assembly by the z-axis support extending through the second slot. The first drive assembly and the second drive assembly being attached to the bottom of the table. The table of support surface is at least as wide as the length of the first slot and the second slot and twice as long as the length of the first slot and the second slot. The support surface may be adjustable, may be mounted on wheels, may be secured to a surface such as a floor, or may comprise legs suitable for contacting the surface. The support surface may also comprise a ribbon of fluoropolymer inert material configured to deflect spills away from the first drive assembly and the second drive assembly and a channel along the periphery of the support surface for collecting potential spillage.

In a further additional embodiment, automated sampling and dispensing device may comprise a first support surface for supporting a sample holder or a plurality of sample holders and a second support surface for supporting a fluid holder or a plurality of fluid holders. The first support surface for supporting the sample holder may comprise the mixing assembly as previously described. Each of the first and the second support surfaces may comprise the aspects of the support surface described in the single support surface embodiment.

The first arm assembly 2002, the second arm assembly 2004, the fluid probe and the sample probe may be substantially similar to sample arm assembly 104 described previously and in FIG. 8. First and second arm assemblies 2002, 2004 may be comprised of carbon fiber material. However, it is contemplated that the first arm assembly, the second arm assembly, the sample probe and the fluid probe may be comprised of any material suitable for use in automatic sampling or dispensing system including aluminum, steel, plastic and the like. The carbon fiber material may be coated with a fluoropolymer inert material. A suction assembly may be attached to the first arm assembly and the second arm assembly. The suction assembly of the first arm assembly may allow the sample to be removed from the sample vessel. The suction assembly of the second arm assembly may allow the fluid to be removed from the fluid container. The automated sampling or dispensing device may further comprise a dispensing system attached to the second arm assembly allowing a fluid to be dispensed into the sample vessel, and a dispensing system attached to the first arm assembly allowing a reagent to be dispensed into the sample vessel. It is further contemplated that a rail may be attached to an edge of the support surface allowing the attachment of additional arm assemblies.

The arm length of the first arm assembly may be no more than one-half the length of possible first drive assembly linear translation along the x-axis. Similarly, the arm length of the second arm assembly may be no more than one-half the length of possible second drive assembly linear translation along the x-axis.

The first drive assembly 128 and the second drive assembly 2028 may be the same as drive assembly 128 described in previously and in FIGS. 2A, 2B, 6 and 7. Particularly, drive assemblies may each comprise a controller 132, a plurality of motors 138-140, a linear drive 134, and a sled 136. A first motor controls translation of the first arm assembly movements and second arm assembly movements along the first slot and the second slot respectively, and are attached to the underside of the support surface. A second motor of each drive assembly controls angular rotation of the first arm assembly and the second arm assembly and is connected to the sled. A third motor of each drive assembly controls movement along the z-axis of the first arm assembly and the second arm assembly and is attached to the sled. In one embodiment, all mechanical operations of the first drive assembly and the second drive assembly occur below the level of the support surface. However, it is contemplated that mechanical operations of the first and second drive assemblies may occur about the level of the support surface.

The first drive assembly and the second drive assembly may each also comprise at least one of a wireless transmitter, receiver or transceiver for communicating with a controller computer. The first drive assembly and the second drive assembly may also be enclosed by a housing configured to protect the first drive assembly and the second drive assembly from dust/debris.

Figure 29:
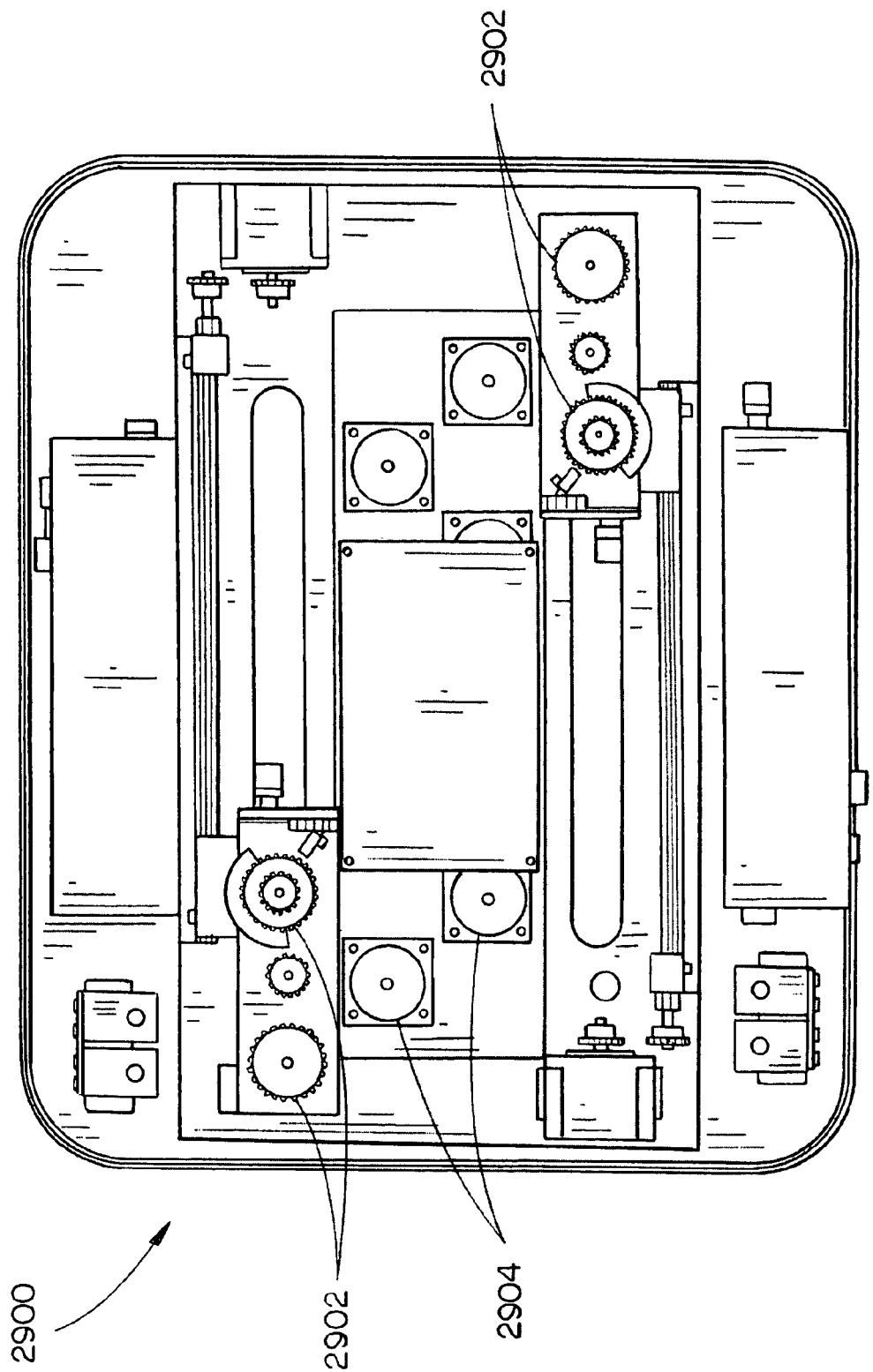
FIG. 29 is a top view of a mixing assembly of an automated sampling or dispensing in accordance with an exemplary embodiment of the present invention.

With specific reference to FIGS. 24 and 25, an isometric view of an automated sampling or dispensing device further comprising at least one mixing assembly 2030 in accordance with an exemplary embodiment of the present invention is shown. In the embodiment shown, automated sampling and dispensing device comprises a plurality of mixing assemblies suitable for selective mixing a sample holder 106. The support surface 102 may further comprise a mixing assembly suitable for mixing the fluid and the sample. Mixing assembly 2030 may be suitable for providing selective rotational, vibrational or like mixing of the fluid and the sample prior to removal of some or the entire sample and fluid solution from the sample holder. It is further contemplated that mixing assembly 2030 may be any assembly suitable for introducing a substantial direction change in the flow of the fluid and sample to thereby induce mixing of the fluid and sample as may be necessary to achieve a sufficient equilibration of the mixed sample and fluid. Referring to FIG. 29, a top view of a mixing assembly 2904 suitable for providing rotational mixing for an automated sampling or dispensing in accordance with an exemplary embodiment of the present invention is shown. Mixing assembly 2904 may comprise at least one motor 2902 suitable for generating rotational motion for mixing assembly 2904. In one embodiment, mixing assembly may comprise a support plate 2032 suitable for coupling with a mixing device 2034 coupled to the support assembly 102. Mixing assembly 2904 be motor or electronically operated and may further comprise a controller (not shown) for controlling the mixing device 2034. Controller may be wire or wirelessly coupled to the mixing device and may further comprise a transmitter and receiver, or transceiver suitable for communicating with a transmitter receiver or transceiver of the mixing device. Controller may also be suitable for controlling the speed and duration of mixing of a sample holder. Mixing assembly 2030 may be suitable for mixing an individual sample vessel, a container or holder containing a plurality of sample vessels, a plurality of sample holders 106 or the entire region of the support table 102 comprising the sample holders. To this end, a support assembly may further comprise a moveable portion suitable for coupling with at least one other support assembly portion and a mixing assembly 2030. Furthermore, device 2000 may comprise a first support assembly for supporting at least one sample holder and a second support assembly for supporting at least one fluid holder.

Figure 30:
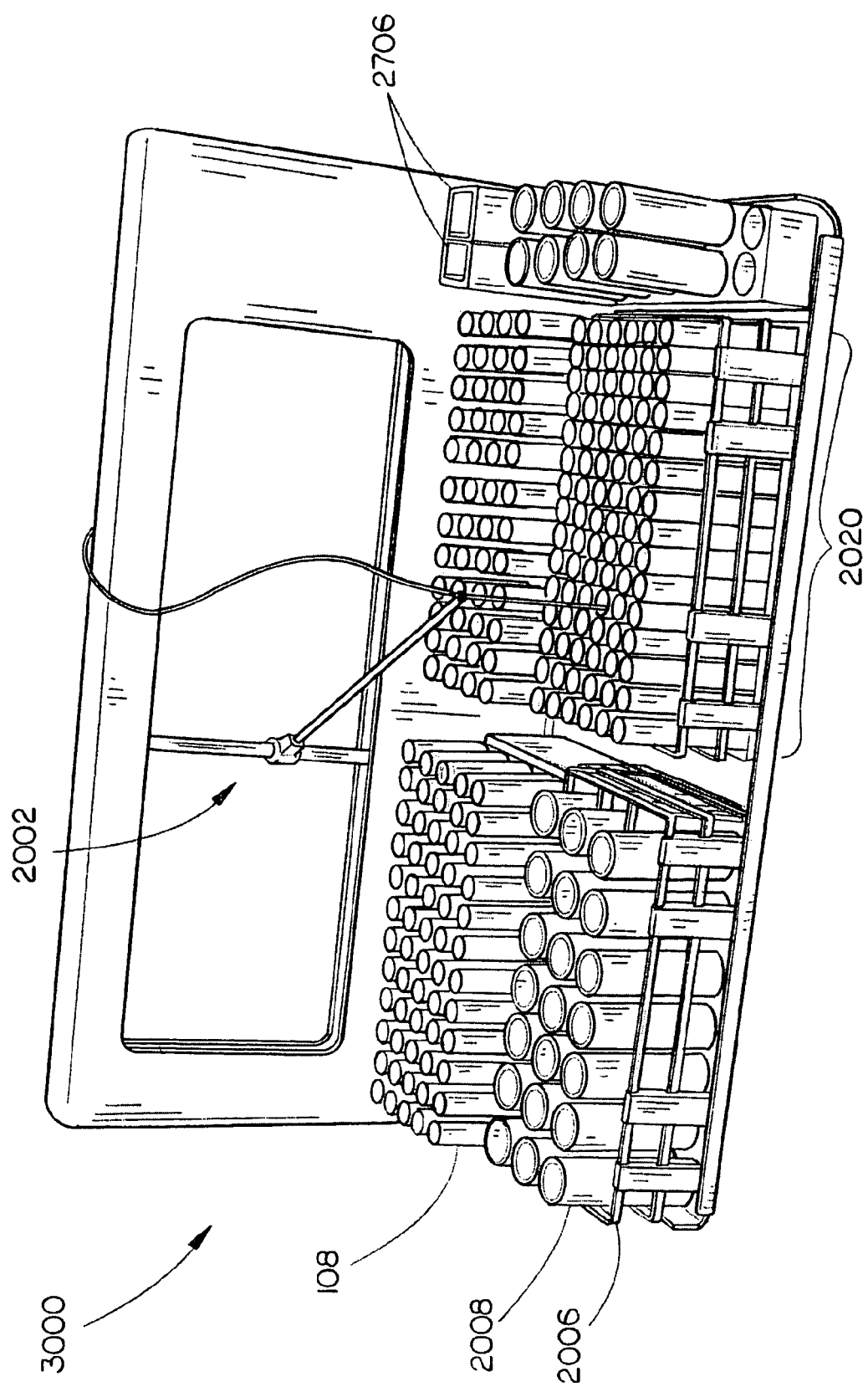
FIG. 30 is an isometric view of a single arm automated sampling or dispensing device in an in accordance with an exemplary embodiment of the present invention.

Referring to FIG. 30, an isometric view of a single arm automated sampling or dispensing device 3000 in an in accordance with an exemplary embodiment of the present invention is shown. Arm assembly may be an arm assembly as describe above in all other embodiments. It is further contemplated that automated sampling or dispensing device may comprise a one arm assembly suitable for collecting fluid from a fluid vessel and depositing the fluid into a sample vessel. In this embodiment, arm assembly may comprise a support surface for supporting a fluid holder and a sample holder, the fluid holder being suitable for holding at least one sample vessel, the sample holder being suitable for holding a sample vessel, an arm assembly for supporting a probe, including a z-axis support and a horizontal probe support arm, a drive assembly coupled to the z-axis support of the arm assembly for powering and positioning the arm assembly, and a mixing assembly coupled to the at least one sample vessel. The arm assembly is suitable for collecting a fluid from the fluid vessel and transferring the fluid to the sample vessel, the mixing assembly is suitable for mixing the fluid and the sample in the at least one sample vessel, and collecting an amount of a mixed fluid and sample solution from the at least one sample vessel.

It is contemplated that any of the automated sampling or dispensing devices considered may comprise a first motor suitable for controlling translation of the arm assembly movements along a first slot and is attached to the underside of the support surface, a second motor controls angular rotation of the arm assembly and is connected to a sled, and a third motor controls movement along a z-axis of the arm assembly and is attached to the sled. The arm assembly and the probe are comprised of carbon fiber material and the carbon fiber material is coated with a fluoropolymer inert material. The automated sampling or dispensing device may further comprise a plurality of rinse stations.

The mixing assembly is a motorized mixing assembly suitable for selectively providing mixing of the fluid and the sample in at least one sample vessel. The mixing assembly is operably coupled to a controller suitable for controlling the speed and duration of mixing of the at least one sample holder. Mixing assembly may provide rotational or vibrational mixing of a fluid and a sample in a sample, or in a common vessel suitable for holding a fluid, a sample or both. Mixing assembly may be coupled to on vessel, a plurality of vessels, a vessel holder, a support surface or the like. No additional mixing implements, such as stirrers, magnetic mixing assemblies, manual rotational mixing, shaking or the like may be necessary. Sample vessels or common mixing vessels may further comprise caps, tops, or a like covering assembly suitable for preventing solution from spilling from the vessel.

In a further additional embodiment, automated sampling or dispensing device probe is suitable for mixing an amount of fluid and a sample in the sample vessel. For instance, the probe may be suitable for bubbling a mixed fluid and sample solution. Bubbling the mixed fluid and sample solution may be accomplished by pushing a gas such as air, argon inert gas, or the like into the mixed fluid and sample solution. Additionally, the probe may be suitable for repeatedly aspirating the mixed fluid and sample solution. To accomplish aspirating or bubbling, the probe may further comprise a valve assembly suitable for selectively dispensing or collecting a fluid, sample or fluid and sample mixture from a fluid vessel or a sample vessel.

Figure 31:
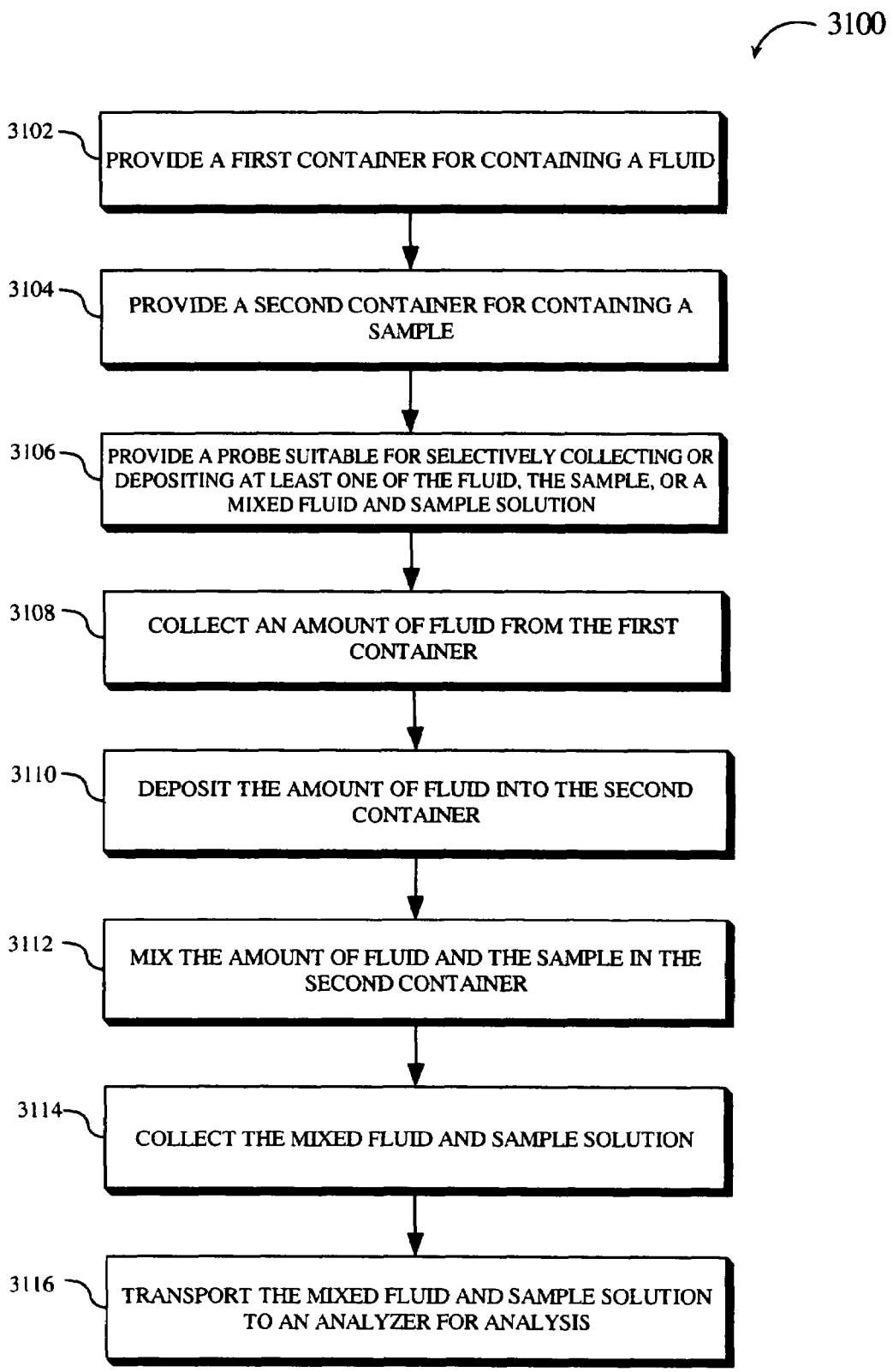
FIG. 31 is a flow diagram illustrating a method for automated sampling or dispensing in accordance with an exemplary embodiment of the present invention.

Referring to FIG. 31, a flow diagram illustrating a method 3100 for automated sampling or dispensing in accordance with an exemplary embodiment of the present invention. Method 3100 may comprise providing a fluid vessel suitable for holding a fluid 3102, providing a sample vessel suitable for holding a sample 3104, providing a probe suitable for selectively collecting or depositing at least one of the fluid, the sample or a mixture of fluid and sample 3106, collecting an amount of fluid from the fluid vessel 3108, depositing the amount of fluid into the sample vessel 3110, mixing the amount of fluid and a sample in the sample vessel 3112, collecting a mixed fluid and sample solution 3114 and transporting the mixed fluid and sample solution to an analyzer for analysis 3116. Components suitable for implementation with method may be all those substantially described in FIGS. 1-30.

In a further additional embodiment, an automated sampling or dispensing system is considered. System may comprise at least one support surface for supporting a sample holder and a fluid holder, the sample holder being suitable for holding a sample vessel, and the fluid holder being suitable for holding a fluid vessel, a first arm assembly for supporting a sample probe, the first arm assembly including a z-axis support and a sample probe support arm, a first drive assembly coupled to the z-axis support of the sample arm assembly for powering and positioning the first arm assembly, a second arm assembly for supporting a fluid probe, the second arm assembly including a z-axis support and a horizontal support arm, a second drive assembly coupled to the z-axis support of the second arm assembly for powering and positioning the second arm assembly, a controller for controlling the first drive assembly and the second drive assembly, and a mixing assembly coupled to the support surface. The first arm assembly is suitable for collecting a sample from a sample container and transferring it to an analyzer. The second arm assembly is suitable for collecting an amount of fluid from the fluid holder and releasing the fluid into a sample container, and the mixing assembly is suitable for mixing the sample and the fluid.

It is believed that the present invention and many of its attendant advantages will be understood by the foregoing description. It is also believed that it will be apparent that various changes may be made in size, materials, shape, form, function, manner of operation, assembly and use of the components thereof without departing from the scope and spirit of the invention or without sacrificing all of its material advantages. The form herein before described being merely an explanatory embodiment thereof. Further, it is contemplated that the specific order or hierarchy of steps in the method can be rearranged while remaining within the scope and spirit of the present invention. It is the intention of the following claims to encompass and include such changes.

What is claimed is:

1. An automated sampling or dispensing device comprising:
    a support surface for supporting a sample holder and a fluid holder, the sample holder being suitable for holding a sample vessel, and the fluid holder being suitable for holding a fluid vessel;
    a first arm assembly for supporting a fluid probe, the first arm assembly including a z-axis support and a horizontal fluid probe support arm;
    a first drive assembly coupled to the z-axis support of the first arm assembly for powering and positioning the first arm assembly;
    a second arm assembly for supporting a sample probe, the second arm assembly including a z-axis support and a horizontal sample probe support arm; and
    a second drive assembly coupled to the z-axis support of the second arm assembly for powering and positioning the second arm assembly; and
    a mixing assembly coupled to the sample holder,
    wherein the first arm assembly is suitable for collecting a fluid from the fluid vessel and transferring the fluid to the sample vessel, the mixing assembly is suitable for mixing the fluid and the sample, and the second arm assembly is suitable for collecting an amount of a mixed fluid and sample solution from the sample vessel, wherein the first drive assembly and the second drive assembly each comprise a controller, a plurality of motors, a linear drive, and a sled, and a first motor of each of the first drive assembly and the second drive assembly controls translation of the first arm assembly movements and second arm assembly movements along the first slot and the second slot and are attached to the underside of the support surface, a second motor of each of the first drive assembly and the second drive assembly controls angular rotation of the first arm assembly and the second arm assembly and is connected to the sled, and a third motor of each of the first drive assembly and the second drive assembly controls movement along the z-axis of the first arm assembly and the second arm assembly and is attached to the sled.

2. An automated sampling or dispensing device comprising:
    a support surface for supporting a sample holder and a fluid holder, the sample holder being suitable for holding a sample vessel, and the fluid holder being suitable for holding a fluid vessel;
    a first arm assembly for supporting a fluid probe, the first arm assembly including a z-axis support and a horizontal fluid probe support arm;
    a first drive assembly coupled to the z-axis support of the first arm assembly for powering and positioning the first arm assembly;
    a second arm assembly for supporting a sample probe, the second arm assembly including a z-axis support and a horizontal sample probe support arm; and
    a second drive assembly coupled to the z-axis support of the second arm assembly for powering and positioning the second arm assembly; and
    a mixing assembly coupled to the sample holder,
    wherein the first arm assembly is suitable for collecting a fluid from the fluid vessel and transferring the fluid to the sample vessel, the mixing assembly is suitable for mixing the fluid and the sample, the second arm assembly is suitable for collecting an amount of a mixed fluid and sample solution from the sample vessel, and substantially all mechanical operations of the first drive assembly and the second drive assembly occur below the level of the support surface.

3. The automated sampling or dispensing device of claim 2, wherein the first drive assembly and the second drive assembly comprise at least one of a wireless transmitter, receiver or transceiver for communicating with a controller computer.

4. The automated sampling or dispensing device of claim 2, further comprising a suction assembly attached to the first arm assembly allowing the fluid to be removed from the fluid vessel.

5. The automated sampling or dispensing device of claim 2, further comprising a suction assembly attached to the second arm assembly allowing the sample to be removed from the sample vessel.

6. The automated sampling or dispensing device of claim 2, further comprising a dispensing assembly attached to the first arm assembly allowing a fluid to be dispensed into the sample vessel.

7. The automated sampling or dispensing device of claim 2, further comprising a plurality of rinse stations.

8. The automated sampling or dispensing device of claim 2, wherein the mixing assembly is a motorized mixing assembly suitable for selectively providing mixing of the fluid and the sample in at least one sample vessel.

9. The automated sampling or dispensing device of claim 8, wherein the motorized mixing assembly is operably coupled to a controller suitable for controlling the speed and duration of mixing of the at least one sample holder.

10. The automated sampling or dispensing device of claim 9, wherein the motorized mixing assembly is a vibrational mixing assembly suitable for selectively providing vibrational motion to at least one sample holder.

11. The automated sampling or dispensing device of claim 9, wherein the motorized mixing assembly is a rotational mixing assembly suitable for selectively providing rotational motion to at least one sample holder.

12. The automated sampling or dispensing device of claim 2, wherein the fluid is comprised of at least one of a standard addition, a diluent, a spike or a calibration solution.

13. The automated sampling or dispensing device of claim 2, wherein at least one of the fluid probe or the sample probe is suitable for mixing an amount of fluid and a sample in the sample vessel.

14. The automated sampling or dispensing device of claim 13, wherein at least one of the fluid probe or the sample probe is suitable for bubbling a mixed fluid and sample solution.

15. The automated sampling or dispensing device of claim 14, wherein the bubbling the mixed fluid and sample solution is accomplished by pushing a gas into the mixed fluid and sample solution.

16. The automated sampling or dispensing device of claim 13, wherein at least one of the fluid probe or the sample probe is suitable for repeatedly aspirating the mixed fluid and sample solution.

17. The automated sampling or dispending device of claim 2, wherein the sample probe further comprises a valve assembly suitable for selectively dispensing or collecting a fluid, sample or fluid and sample mixture from a fluid vessel or a sample vessel.

18. An automated sampling or dispensing device, comprising:
- a support surface for supporting a sample holder and a fluid holder, the sample holder being suitable for holding a sample vessel, and the fluid holder being suitable for holding a fluid vessel;
- a first arm assembly for supporting a fluid probe, the first arm assembly including a z-axis support and a horizontal fluid probe support arm;
- a first drive assembly coupled to the z-axis support of the first arm assembly for powering and positioning the first arm assembly;
- a second arm assembly for supporting a sample probe, the second arm assembly including a z-axis support and a horizontal sample probe support arm; and
- a second drive assembly coupled to the z-axis support of the second arm assembly for powering and positioning the second arm assembly; and
- a mixing assembly coupled to the sample holder,
- wherein a first motor of each of the first drive assembly and the second drive assembly controls translation of the first arm assembly movements and second arm assembly movements along a first slot and a second slot and are attached to the underside of the support surface, a second motor of each of the first drive assembly and the second drive assembly controls angular rotation of the first arm assembly and the second arm assembly and is connected to a sled, and a third motor of each of the first drive assembly and the second drive assembly controls movement along a z-axis of the first arm assembly and the second arm assembly and is attached to the sled.

19. An automated sampling or dispensing device, comprising:
- a support surface for supporting a sample holder and a fluid holder, the sample holder being suitable for holding a sample vessel, and the fluid holder being suitable for holding a fluid vessel;
- a first arm assembly for supporting a fluid probe, the first arm assembly including a z-axis support and a horizontal fluid probe support arm;
- a first drive assembly coupled to the z-axis support of the first arm assembly for powering and positioning the first arm assembly;
- a second arm assembly for supporting a sample probe, the second arm assembly including a z-axis support and a horizontal sample probe support arm; and
- a second drive assembly coupled to the z-axis support of the second arm assembly for powering and positioning the second arm assembly; and
- a mixing assembly coupled to the support surface further comprising a support plate and a mixing device, the mixing assembly configured to substantially mix at least a portion of the fluid and a sample in the sample vessel,
- wherein the sample probe further comprises a valve assembly suitable for selectively dispensing or collecting a fluid, a sample or a fluid and sample mixture from a fluid vessel or a sample vessel, first arm assembly is suitable for collecting a fluid from the fluid vessel and transferring the fluid to the sample vessel, the mixing assembly is suitable for mixing the fluid and the sample, and the second arm assembly is suitable for collecting an amount of a mixed fluid and sample solution from the sample vessel.

\* \* \* \* \*